US007858355B2

(12) United States Patent
Sarcabal et al.

(10) Patent No.: US 7,858,355 B2
(45) Date of Patent: Dec. 28, 2010

(54) DIMERIC GLYCEROL DEHYDRATASES

(75) Inventors: Patricia Sarcabal, Toulouse (FR); Christian Croux, Castanet Tolosan (FR); Philippe Soucaille, Deyme (FR)

(73) Assignees: Institut National de la Recherche Agronomique, Paris (FR); Institut National des Sciences Appliquées de Toulouse, Toulouse (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 12/651,899

(22) Filed: Jan. 4, 2010

(65) Prior Publication Data

US 2010/0129892 A1 May 27, 2010

Related U.S. Application Data

(60) Division of application No. 11/839,455, filed on Aug. 15, 2007, now Pat. No. 7,695,943, which is a division of application No. 10/043,639, filed on Jan. 9, 2002, now Pat. No. 7,267,972, which is a continuation of application No. PCT/FR00/01981, filed on Jul. 7, 2000.

(30) Foreign Application Priority Data

Jul. 9, 1999 (FR) .................................. 99 08939

(51) Int. Cl.

| | |
|---|---|
| ***C12N 9/88*** | (2006.01) |
| ***C12N 9/00*** | (2006.01) |
| ***C12N 1/20*** | (2006.01) |
| ***C12N 15/00*** | (2006.01) |
| ***C12P 7/02*** | (2006.01) |
| ***C07H 21/04*** | (2006.01) |

(52) U.S. Cl. ....................... 435/232; 435/155; 435/183; 435/252.3; 435/320.1; 536/23.2

(58) Field of Classification Search ....................... None
See application file for complete search history.

(56) References Cited

U.S. PATENT DOCUMENTS

| | | | | |
|---|---|---|---|---|
| 5,633,362 | A | 5/1997 | Nagarajan et al. | 536/23.1 |
| 5,686,276 | A | 11/1997 | Laffend et al. | 435/158 |
| 5,821,092 | A | 10/1998 | Nagarajan et al. | 435/158 |
| 7,267,972 | B2 | 9/2007 | Sarcabal et al. | 435/58 |
| 2009/0029431 | A1 | 1/2009 | Sarcabal et al. | 435/155 |

FOREIGN PATENT DOCUMENTS

WO WO 98/21339 5/1998

OTHER PUBLICATIONS

Chica et al. Curr Opin Biotechnol. Aug. 2005;16(4):378-84.*

Sen et al. Appl Biochem Biotechnol. Dec. 2007;143(3):212-23.*

Chica et al., "Semi-rational approach to engineering enzyme activity: combining the benefits of directed evolution and rational design," *Curr. Opin. Biotechnol.*, 16 (4): 378-384, 2005.

Luers et al., "Glycerol conversion to 1,3-propanediol by *Clostridium pasteurianum*: cloning and expression of the gene encoding 1,3-propanediol dehydrogenase," *FEMS Microbiology Letters*, 154:337-345, 1997.

Macis et al., "Properties and sequences of the coenzyme $B_{12}$-dependent glycerol dehydratase of *Clostridium pasteurianum*," *FEMS Microbiology Letters*, 164:21-28, 1998.

Office Action, issued in U.S. Appl. No. 10/043,639, mailed Nov. 1, 2006.

Office Action, issued in U.S. Appl. No. 10/043,639, mailed Apr. 20, 2006.

Office Action, issued in U.S. Appl. No. 10/043,639, mailed Jul. 29, 2005.

Office Action, issued in U.S. Appl. No. 10/043,639, mailed Mar. 31, 2005.

Office Action, issued in U.S. Appl. No. 10/043,639, mailed Jun. 23, 2004.

Office Action, issued in U.S. Appl. No. 11/839,455, mailed Feb. 20, 2009.

Reimann et al., "1,3-propanediol formation with product-tolerant mutants of *Costridium butyricum* DSM 5431 in continuous culture: productivity, carbon and electron flow," *J. Applied Microbiology*, 84:1125-1130, 1998.

Sen et al., "Developments in directed evolution for improving enzyme functions," *Appl. Biochem. Biotechnol.*, 143 (3): 212-223, 2007.

Skraly et al., "Construction and characterization of a 1,3-propanediol operon," *Applied and Environmental Microbiology*, 64(1):98-105, 1998.

Weidner and Sawers, "Molecular characterization of the genes encoding pyruvate formate-lyase and its activating enzyme of *Clostridium pasteurianum*," *J. of Bacteriology*, 178(8):2440-2444, 1996.

Raynaud et al., "Molecular characterization of the 1,3-propanediol (1,3-PD) operon of *Clostridium butyricum*," *Proc. Natl. Acad. Sci. USA*, 100(9):5010-5015, 2003.

Seyfried et al., "Cloning, sequencing, and overexpression of the genes encoding coenzyme $B_{12}$-dependent glycerol dehydratase of *Citrobacter freundii*," *Journal of Bacteriology*, 178(19):5793-5796, 1996.

* cited by examiner

*Primary Examiner*—Christian L Fronda
(74) *Attorney, Agent, or Firm*—Fulbright & Jaworski L.L.P.

(57) ABSTRACT

The invention concerns a method for preparing 1,3-propanediol from a carbon-containing substance, said method comprising a step which consists in culturing a recombinant micro-organism not producing coenzyme B12 in the absence of coenzyme B12 or one of its precursors. The invention also concerns a nucleic acid coding for a glycerol dehydratase whereof the catalytic activity is independent of the presence of coenzyme B12 or one of its precursors and a nucleic acid coding for a 1,3-propanol dehydrogenase intervening in the synthesis of 1,3-propanediol. The invention further concerns recombinant vectors and host cells comprising said nucleic acids and the polypeptides coded by the latter.

6 Claims, 10 Drawing Sheets

| ○ | Biomass (O.D. 620 nm) |
| □ | Glucose |
| △ | Acetate |
| ▽ | Butyrate |
| ● | 1,3-propanediol |

SEQUENCE LISTING

```
<160> NUMBER OF SEQ ID NOS: 14

<210> SEQ ID NO 1
<211> LENGTH: 2364
<212> TYPE: DNA
<213> ORGANISM: Clostridium butyricum
```

-continued

<400> SEQUENCE: 1

```
atgataagta aaggatttag tacccaaaca gaaagaataa atattttaaa ggctcaaata     60
ttaaatgcta aaccatgtgt tgaatcagaa agagcaatat taataacaga atcatttaaa    120
caaacagaag gccagccagc aattttaaga agagcattgg cattgaaaca catacttgaa    180
aatatcccta taacaattag agatcaagaa cttatagtgg gaagtttaac taaagaacca    240
aggtcttcac aagtatttcc tgagttttct aataagtggt tacaagatga attggataga    300
ttaaataaga gaactggaga tgcattccaa atttcagaag aaagtaaaga aaaattaaaa    360
gatgtctttg agtattggaa tggaaagaca acaagtgagt tagcaacttc atatatgaca    420
gaggaaacaa gagaggcagt aaattgtgaa gtatttactg taggaaacta ctattataat    480
ggcgtaggac atgtatctgt agattatgga aaagtattaa gggttggatt taatgggatt    540
ataaatgagg ctaaggaaca attagaaaaa aacaggagta tagatcctga ttttataaag    600
aaagaaaaat tcctaaatag tgttattatc tcatgcgaag ctgcaataac atatgtaaat    660
agatatgcta aaaaggctaa agagattgca gataatacaa gtgatgcaaa aagaaaagct    720
gaattaaatg aaatagcaaa aatttgttca aaagtttcag gagagggagc taaatctttc    780
tatgaagcat gtcaattatt ttggtttatt catgcaataa taaatataga atctaatgga    840
cattctattt ctccagctag atttgatcaa tacatgtatc catattatga aaatgataaa    900
aatataacag ataagtttgc tcaagaatta atagattgta tctggattaa attaaatgat    960
attaataaag taagagatga gatttcaact aaacattttg gtggttaccc aatgtatcaa   1020
aaattaattg ttgggggtca aaattcagaa ggaaaagatg caactaataa agtatcatat   1080
atggcattag aagcagctgt ccatgtaaag ttgcctcagc catctttgtc agtaagaata   1140
tggaataaga ctccagatga atttttgctt agagcagcag aattaactag agaagggtta   1200
ggacttcctg cttattataa tgatgaagtt attattccag cattagtttc tagaggtctt   1260
acattagaag atgcaagaga ctacggaata attggatgtg ttgaaccaca aaagccagga   1320
aaaacagaag gatggcatga ttcagcattc tttaatcttg caagaatagt agagttaact   1380
ataaattctg gatttgataa aaataaacag attggaccta aaactcaaaa ttttgaagaa   1440
atgaaatcct ttgatgaatt catgaaagct tataaagctc aaatggagta ttttgtaaaa   1500
catatgtgct gtgctgataa ttgcatagat attgcacatg cagaaagagc tccattacct   1560
ttcttgtcat caatggttga taattgtatc ggaaaaggaa agagccttca agatggtggt   1620
gcagaatata acttcagtgg accacaaggt gttggagtag ctaatattgg agattcatta   1680
gttgcagtta aaaaaattgt gtttgatgaa aataagatta ctccttcaga attaaagaaa   1740
acattaaata atgattttaa aaattcagaa gaaatacaag ccttactaaa aaatgctcct   1800
aagtttggaa atgatattga tgaagttgat aatttagcta gagagggtgc attagtatac   1860
tgtagagaag ttaataaata tacaaatcca aggggaggaa attttcaacc aggattatat   1920
ccatcttcaa ttaatgtata ttttggaagc ttaacaggtg ctactccaga tggaaggaaa   1980
tccggacaac cattagctga tggggtttct ccatcaagag gctgtgatgt atctggacct   2040
actgcagctt gtaactcagt tagtaaatta gatcatttta tagcttcaaa tggaacttta   2100
tttaatcaaa aattccatcc gtcagcatta aaaggtgata atggattaat gaatttatca   2160
tcattaataa gaagttattt tgatcaaaag ggatttcatg ttcaatttaa tgtaatagat   2220
aaaaaaatat tacttgcagc acaaaaaaat cctgaaaaat atcaagattt aattgttaga   2280
```

-continued gttgcaggat atagtgcaca gttcatttct ttagataaat ctattcaaaa tgatattatt 2340
gcaagaactg aacatgttat gtaa 2364

<210> SEQ ID NO 2
<211> LENGTH: 915
<212> TYPE: DNA
<213> ORGANISM: Clostridium butyricum

<400> SEQUENCE: 2
atgagtaagg agataaaagg cgttttattt aacatacaaa aattttcgtt acatgatggg 60
cctggaataa gaactatagt attttttaag ggatgttcaa tgtcgtgctt atggtgcagt 120
aatccagaat cccaagatat taaacctcaa gtaatgttta ataaaaattt atgtacaaaa 180
tgtggaagat gtaaatctca atgtaaaagt gcaggtattg atatgaattc agaatatagg 240
atagataaaa gcaaatgtac agagtgtaca aaatgtgttg ataattgctt aagcggggca 300
cttgttattg aaggaaggaa ttacagtgtt gaagacgtta taaaggaatt gaaaaaagat 360
agtgttcaat atagaagatc aaacggtgga attacactat ctggaggggga agtattactt 420 caaccagatt ttgcagtgga gcttttaaaa gagtgtaaat catatggctg gcacactgcc 480
attgaaacag caatgtatgt taatagtgaa tctgtaaaaa aagtaattcc atatatagat 540
ctggctatga ttgatataaa aagtatgaat gatgaaatcc ataggaaatt tacaggagtg 600
agtaacgaaa taatattaca aaacattaaa ttaagtgatg aattagctaa agaaataata 660
atcagaattc ctgtaataga aggatttaat gcagatttac aaagtatagg agcaatagct 720
caattttcaa aatcattaac aaatcttaaa agaatagatc ttcttccata ccataattat 780
ggagaaaata agtatcaagc aattggaaga gagtattctt tgaaagaact aaaatcacct 840
agtaaagaca aaatggaaag attaaaagct ttagttgaaa tcatgggaat accgtgcaca 900
attggagctg agtaa 915

<210> SEQ ID NO 3
<211> LENGTH: 28
<212> TYPE: DNA
<213> ORGANISM: Clostridium butyricum

<400> SEQUENCE: 3
tagataaaac aaacaaaaat gttattat 28

<210> SEQ ID NO 4
<211> LENGTH: 1158
<212> TYPE: DNA
<213> ORGANISM: Clostridium butyricum

<400> SEQUENCE: 4
atgagaatgt atgattattt agtaccaagt gtaaacttta tgggagcaaa ttcagtatca 60
gtagtaggtg aaagatgcaa aatattaggt ggaaaaaaag cattgatagt tacagataag 120
tttctaaaag atatggaagg tggagctgtt gaattaacag ttaaatattt aaaagaagct 180
ggattagatg ttgtatatta tgacggagtt gaaccaaatc caaaagatgt taatgttata 240
gaaggattaa aaatatttaa agaagaaaat tgtgacatga tagtaactgt aggtggagga 300
agttcgcatg attgcggtaa gggaatagga attgctgcaa cacatgaagg agatctttat 360
gattatgcag gaatagaaac acttgtcaat ccattgccac caatagtagc tgtaaatact 420
actgcaggaa ctgctagtga attaactcgt cattgtgtat tgactaatac aaaaaagaaa 480
ataaaatttg ttatagttag ctggagaaat ttgcctctag tatctataaa tgatccaatg 540

-continued

```
cttatggtca aaaaacctgc aggattaaca gcagctacag gaatggatgc tttaacacat    600

gcaatagaag catatgtatc aaaagatgca aatccagtaa cagatgcttc agcaatacaa    660

gctattaaat taatttcaca aaatttaaga caagctgtag ctttaggaga aaatcttgaa    720

gcaagagaaa atatggctta tgcatcatta ctagcaggaa tggcatttaa taatgctaat    780

ttaggatatg tacatgcaat ggctcatcaa ttagggggac tgtatgatat ggcacatggt    840

gttgctaatg caatgctatt accacatgtt gaacgttata atatgctatc aaatcctaag    900

aagtttgcag atatagcaga atttatggga gaaaatatat ctggactttc tgtaatggaa    960

gcagcagaga aagccataaa tgcaatgttc aggctttcag aggatgttgg aattccgaaa   1020

agtctaaagg agatgggagt gaaacaagaa gattttgagc atatggcaga actagctctt   1080

ttagatggaa atgcctttag caatccaaga aaaggaaatg caaaagatat tataaatatt   1140

tttaaggctg cttattaa                                                 1158
```

<210> SEQ ID NO 5
<211> LENGTH: 4963
<212> TYPE: DNA
<213> ORGANISM: Clostridium butyricum

<400> SEQUENCE: 5

```
gaataaaagt tatctataaa tgataaaagt cattattaga taacttttta ttttaaaata     60

actactaata aaaagttcaa agaatattac agtagacatt tgaaagaatg caatgataaa    120

caattgtatt agttttaact ttagataaaa caaacaaaaa tgttattatt agccaagaaa    180

atactgttac aaaagaaaag agaaaaacat agcaaaagag taccaatatt aagcaataaa    240

gtttgttaaa atattatcaa taaaatgata agattagata aaccaagtaa gaatgtgatt    300

ggaggagtaa aaatgataag taaaggattt agtacccaaa cagaaagaat aaatatttta    360

aaggctcaaa tattaaatgc taaaccatgt gttgaatcag aaagagcaat attaataaca    420

gaatcattta aacaaacaga aggccagcca gcaattttaa gaagagcatt ggcattgaaa    480

cacatacttg aaaatatccc tataacaatt agagatcaag aacttatagt gggaagttta    540

actaaagaac cagatgcttc acaagtattt cctgagtttt ctaataagtg gttacaagat    600

gaattggata gattaaataa gagaactgga gatgcattcc aaatttaaga agaaagtaaa    660

gaaaaattaa aagatgtctt tgagtattgg aatggaaaga caacaagtga gttagcaact    720

tcatatatga cagaggaaac aaaagatgca gtaaattgtg aagtatttac tgtaggaaac    780

tactattata atggcgtagg acatgtatct gtagattatg gaaaagtatt aagggttgga    840

tttaatggga ttataaatga ggctaaggaa caattagaaa aaaacaggag tatagatcct    900

gattttataa agaaagaaaa attcctaaat agtgttatta tctcatgcga agctgcaata    960

acatatgtaa atagatatgc taaaaaggct aaagagattg cagataatac aaaagatgca   1020

aaaagaaaag ctgaattaaa tgaaatagca aaaatttgtt caaaagatac aggagaggga   1080

gctaaatctt tctatgaagc atgtcaatta ttttggttta tacatgcaat aataaatata   1140

gaatctaatg gacattctat ttctccagct agatttgatc aatccagtaa tccatattat   1200

gaaaatgata agaatattac agataagttt gctattaaat taatagattg taattggatt   1260

aaattaaatg atattaataa agtaagagat gagatttcaa ctaaacattt tggtggttac   1320

catatgtatc aaaaattaat tgttgggggt caaaattcag aaggaaaaga tgcaactaat   1380

aaagtatcat atatggcttt agaagcagct gtccatgtaa agttgcctca gccatctttg   1440
```

-continued

```
tcagtaagaa tatggaataa gactccagat gattttgagc ttagagcagc aggattaact   1500
agagaagggt taggacttcc tgcttattat aatgatgaag ttattattcc agcattagtt   1560
tctagaggtc ttacattaga atatagcaga gactacggaa taattggatg tgttgaacca   1620
caaaagccag gaaaaacaga aggatggcat gattatgcat tctttaatct tgaaagaata   1680
gtagagttaa ctataaattc tggatttgat aaaaaagaac agattggacc taaaactcaa   1740
aattttgaag aaaggaaatc ctttgatgaa ttcatgaaag cttataaagc tcaaatggag   1800
tattttgtaa aacatatgtg ctgtgctgat aaatgataag atattgcaca tgcagaaaga   1860
gctccattac ctttcttgtc accacatgtt gataattgta tcggaaaagg aaagagcaat   1920
caagctgtag gtgcagaata taacttcagt ggaccacaag gtgttggagt agctaatatt   1980
ggagattcat tagttgcagt taaaaaaatt gtgtttgatg aaaataagat tactccttca   2040
gaattaaaga aaacattaaa taatgatttt aaaaattcag aagaaataca agccttacta   2100
aaaaatgctc ctaagtttgg aaatgatatt gatgaagttg ataatttagc tagagagggt   2160
gcattagtat actgtagaga agttaataaa tatacaaatc caaggggagg aaattttcaa   2220
ccaggattat atccatcttc aattaatgta tattttggaa gcttaacagg tgctactcca   2280
gatggaagga aatccggaca accattagct gatggggttt ctccatcaag aggctgtgat   2340
gtatctggac ctactgcagc ttgtaactca gttagtaaat tagatcattt tatagcttca   2400
aatggaactt tatttaatca aaaattccat ccgtcagcat taaaaggtga taatggatta   2460
atgaatttat catcattaat aagaagttat tttgatcaaa agggatttca tgttcaattt   2520
aatgtaatag ataaaaaaat attacttgca gcacaaaaaa atcctgaaaa atatcaagat   2580
ttaattgtta gagttgcagg atatagtgca cagttcattt ctttagataa atctattcaa   2640
aatgatatta ttgcaagaac tgaacatgtt atgtaaagac agcttttaaa ggggataaaa   2700
gtaatgagta aggagataaa aggcgtttta tttaacatac aaaaattttc gttacatgat   2760
gggcctggaa taagaactat agtatttttt aagggatgtt caatgtcgtg cttatggtgc   2820
agtaatccag aatcccaaga tattaaacct caagtaatgt ttaataaaaa tttatgtaca   2880
aaatgtggaa gatgtaaatc tcaatgtaaa agtgcaggta ttgatatgaa ttcagaatat   2940
aggatagata aaagcaaatg tacagagtgt acaaaatgtg ttgataattg cttaagcggg   3000
gcacttgtta ttgaaggaag gaattacagt gttgaagacg ttataaagga attgaaaaaa   3060
gatagtgttc aatatagaag atcaaacggt ggaattacac tatctggagg ggaagtatta   3120
cttcaaccag attttgcagt ggagctttta aaagagtgta aatcatatgg ctggcacact   3180
gccattgaaa cagcaatgta tgttaatagt gaatctgtaa aaaaagtaat tccatatata   3240
gatctggcta tgattgatat aaaaagtatg aatgatgaaa tccataggaa atttacagga   3300
gtgagtaacg aaataatatt acaaaacatt aaattaagtg atgaattagc taaagaaata   3360
ataatcagaa ttcctgtaat agaaggattt aatgcagatt tacaaagtat aggagcaata   3420
gctcaatttt caaaatcatt aacaaatctt aaaagaatag atcttcttcc ataccataat   3480
tatggagaaa ataagtatca agcaattgga agagagtatt ctttgaaaga actaaaatca   3540
cctagtaaag acaaaatgga aagattaaaa gctttagttg aaatcatggg aataccgtgc   3600
acaattggag ctgagtaata gtagctttac atcagatatt ttaaaaacaa ttttaaatta   3660
aaaggagaag attgcatatg agaatgtatg attatttagt accaagtgta aactttatgg   3720
gagcaaattc agtatcagta gtaggtgaaa gatgcaaaat attaggtgga aaaaaagcat   3780
tgatagttac agataagttt ctaaaagata tggaaggtgg agctgttgaa ttaacagtta   3840
```

-continued

```
aatatttaaa agaagctgga ttagatgttg tatattatga cggagttgaa ccaaatccaa   3900

aagatgttaa tgttatagaa ggattaaaaa tatttaaaga agaaaattgt gacatgatag   3960

taactgtagg tggaggaagt tcgcatgatt gcggtaaggg aataggaatt gctgcaacac   4020

atgaaggaga tctttatgat tatgcaggaa tagaaacact tgtcaatcca ttgccaccaa   4080

tagtagctgt aaatactact gcaggaactg ctagtgaatt aactcgtcat tgtgtattga   4140

ctaatacaaa aaagaaaata aaatttgtta tagttagctg gagaaatttg cctctagtat   4200

ctataaatga tccaatgctt atggtcaaaa aacctgcagg attaacagca gctacaggaa   4260

tggatgcttt aacacatgca atagaagcat atgtatcaaa agatgcaaat ccagtaacag   4320

atgcttcagc aatacaagct attaaattaa tttcacaaaa tttaagacaa gctgtagctt   4380

taggagaaaa tcttgaagca agagaaaata tggcttatgc atcattacta gcaggaatgg   4440

catttaataa tgctaattta ggatatgtac atgcaatggc tcatcaatta gggggactgt   4500

atgatatggc acatggtgtt gctaatgcaa tgctattacc acatgttgaa cgttataata   4560

tgctatcaaa tcctaagaag tttgcagata tagcagaatt tatgggagaa aatatatctg   4620

gactttctgt aatggaagca gcagagaaag ccataaatgc aatgttcagg ctttcagagg   4680

atgttggaat tccgaaaagt ctaaaggaga tgggagtgaa acaagaagat tttgagcata   4740

tggcagaact agctctttta gatggaaatg cctttagcaa tccaagaaaa ggaaatgcaa   4800

aagatattat aaatattttt aaggctgctt attaattaat actatttaaa ggattcaaag   4860

taaaagataa aagatatata tattagattt aagattttat tataggctaa caacaaagaa   4920

caagttaagt attaaactta gcttgttctt tgttgtttat ttt                      4963
```

<210> SEQ ID NO 6
<211> LENGTH: 783
<212> TYPE: PRT
<213> ORGANISM: Clostridium butyricum

<400> SEQUENCE: 6

```
Met Ile Ser Lys Gly Phe Ser Thr Thr Glu Arg Ile Asn Ile Leu Lys
1               5                   10                  15

Ala Gln Ile Leu Asn Ala Lys Pro Cys Val Glu Ser Glu Arg Ala Ile
            20                  25                  30

Leu Ile Thr Glu Ser Phe Lys Gln Thr Gly Gln Pro Ala Ile Leu Arg
        35                  40                  45

Arg Ala Leu Ala Leu Lys His Ile Leu Glu Asn Ile Pro Ile Thr Ile
    50                  55                  60

Arg Asp Gln Glu Leu Ile Val Gly Ser Leu Thr Lys Glu Pro Arg Ser
65                  70                  75                  80

Ser Gln Val Phe Pro Glu Phe Ser Asn Lys Trp Leu Gln Asp Glu Leu
                85                  90                  95

Asp Arg Leu Asn Lys Arg Thr Gly Asp Ala Phe Gln Ile Ser Glu Glu
            100                 105                 110

Ser Lys Glu Lys Leu Lys Asp Val Phe Glu Tyr Trp Asn Gly Lys Thr
        115                 120                 125

Thr Ser Glu Leu Ala Thr Ser Tyr Met Thr Glu Glu Thr Arg Glu Ala
    130                 135                 140

Val Asn Cys Glu Val Phe Thr Val Gly Asn Tyr Tyr Tyr Asn Gly Val
145                 150                 155                 160

Gly His Val Ser Val Asp Tyr Lys Val Leu Arg Val Gly Phe Asn Gly
                165                 170                 175
```

-continued

```
Ile Ile Asn Glu Ala Lys Glu Gln Leu Glu Lys Asn Arg Ser Asp Pro
            180                 185                 190

Asp Phe Ile Lys Lys Glu Lys Phe Leu Asn Ser Val Ile Ile Ser Cys
        195                 200                 205

Glu Ala Ala Ile Thr Tyr Val Asn Arg Tyr Ala Lys Lys Ala Lys Glu
    210                 215                 220

Ile Ala Asp Asn Thr Ser Asp Ala Lys Arg Lys Ala Glu Leu Asn Glu
225                 230                 235                 240

Ile Ala Lys Ile Cys Ser Lys Val Ser Gly Glu Gly Ala Lys Ser Phe
                245                 250                 255

Tyr Glu Ala Cys Gln Leu Phe Trp Phe Ile His Ala Ile Ile Asn Ile
            260                 265                 270

Glu Ser Asn Gly His Ser Ile Ser Pro Ala Arg Phe Asp Gln Tyr Met
        275                 280                 285

Tyr Pro Tyr Tyr Glu Asn Asp Lys Asn Ile Thr Asp Lys Phe Ala Gln
    290                 295                 300

Glu Leu Ile Asp Cys Ile Trp Ile Lys Leu Asn Asp Ile Asn Lys Val
305                 310                 315                 320

Arg Asp Glu Ile Ser Thr Lys His Phe Gly Gly Tyr Pro Met Tyr Gln
                325                 330                 335

Lys Leu Ile Val Gly Gly Gln Asn Ser Glu Gly Lys Asp Ala Thr Asn
            340                 345                 350

Lys Val Ser Tyr Met Ala Leu Glu Ala Ala Val His Val Lys Leu Pro
        355                 360                 365

Gln Pro Ser Leu Ser Val Arg Ile Trp Asn Lys Thr Pro Asp Glu Phe
    370                 375                 380

Leu Leu Arg Ala Ala Glu Leu Thr Arg Glu Gly Leu Gly Leu Pro Ala
385                 390                 395                 400

Tyr Tyr Asn Asp Glu Val Ile Ile Pro Ala Leu Val Ser Arg Gly Leu
                405                 410                 415

Thr Leu Glu Asp Ala Arg Asp Tyr Gly Ile Ile Gly Cys Val Glu Pro
            420                 425                 430

Gln Lys Pro Gly Lys Thr Glu Gly Trp His Asp Ser Ala Phe Phe Asn
        435                 440                 445

Leu Ala Arg Ile Val Glu Leu Thr Ile Asn Ser Gly Phe Asp Lys Asn
    450                 455                 460

Lys Gln Ile Gly Pro Lys Thr Gln Asn Phe Glu Glu Met Lys Ser Phe
465                 470                 475                 480

Asp Glu Phe Met Lys Ala Tyr Lys Ala Gln Met Glu Tyr Phe Val Lys
                485                 490                 495

His Met Cys Cys Ala Asp Asn Cys Ile Asp Ile Ala His Ala Glu Arg
            500                 505                 510

Ala Pro Leu Pro Phe Leu Ser Ser Met Val Asp Asn Cys Ile Gly Lys
        515                 520                 525

Gly Lys Ser Leu Gln Asp Gly Gly Ala Glu Tyr Asn Phe Ser Gly Pro
    530                 535                 540

Gln Gly Val Gly Val Ala Asn Ile Gly Asp Ser Leu Val Ala Val Lys
545                 550                 555                 560

Lys Ile Val Phe Asp Glu Asn Lys Ile Thr Pro Ser Glu Leu Lys Lys
                565                 570                 575

Thr Leu Asn Asn Asp Phe Lys Asn Ser Glu Glu Ile Gln Ala Leu Leu
            580                 585                 590
```

-continued

Lys Asn Ala Pro Lys Phe Gly Asn Asp Ile Asp Glu Val Asp Asn Leu
595 600 605

Ala Arg Glu Gly Ala Leu Val Tyr Cys Arg Glu Val Asn Lys Tyr Thr
610 615 620

Asn Pro Arg Gly Gly Asn Phe Gln Pro Gly Leu Tyr Pro Ser Ser Ile
625 630 635 640

Asn Val Tyr Phe Gly Ser Leu Thr Gly Ala Thr Pro Asp Gly Arg Lys
645 650 655

Ser Gly Gln Pro Leu Ala Asp Gly Val Ser Pro Ser Arg Gly Cys Asp
660 665 670

Val Ser Gly Pro Thr Ala Ala Cys Asn Ser Val Ser Lys Leu Asp His
675 680 685

Phe Ile Ala Ser Asn Gly Thr Leu Phe Asn Gln Lys Phe His Pro Ser
690 695 700

Ala Leu Lys Gly Asp Asn Gly Leu Met Asn Leu Ser Ser Leu Ile Arg
705 710 715 720

Ser Tyr Phe Asp Gln Lys Gly Phe His Val Gln Phe Asn Val Ile Asp
725 730 735

Lys Lys Ile Leu Leu Ala Ala Gln Lys Asn Pro Glu Lys Tyr Gln Asp
740 745 750

Leu Ile Val Arg Val Ala Gly Tyr Ser Ala Gln Phe Ile Ser Leu Asp
755 760 765

Lys Ser Ile Gln Asn Asp Ile Ile Ala Arg Thr Glu His Val Met
770 775 780

<210> SEQ ID NO 7
<211> LENGTH: 304
<212> TYPE: PRT
<213> ORGANISM: Clostridium butyricum

<400> SEQUENCE: 7

Met Ser Lys Glu Ile Lys Gly Val Leu Phe Asn Ile Gln Lys Phe Ser
1 5 10 15

Leu His Asp Gly Pro Gly Ile Arg Thr Ile Val Phe Phe Lys Gly Cys
20 25 30

Ser Met Ser Cys Leu Trp Cys Ser Asn Pro Glu Ser Gln Asp Ile Lys
35 40 45

Pro Gln Val Met Phe Asn Lys Asn Leu Cys Thr Lys Cys Gly Arg Cys
50 55 60

Lys Ser Gln Cys Lys Ser Ala Gly Ile Asp Met Asn Ser Glu Tyr Arg
65 70 75 80

Ile Asp Lys Ser Lys Cys Thr Glu Cys Thr Lys Cys Val Asp Asn Cys
85 90 95

Leu Ser Gly Ala Leu Val Ile Glu Gly Arg Asn Tyr Ser Val Glu Asp
100 105 110

Val Ile Lys Glu Leu Lys Lys Asp Ser Val Gln Tyr Arg Arg Ser Asn
115 120 125

Gly Gly Ile Thr Leu Ser Gly Gly Glu Val Leu Leu Gln Pro Asp Phe
130 135 140

Ala Val Glu Leu Leu Lys Glu Cys Lys Ser Tyr Gly Trp His Thr Ala
145 150 155 160

Ile Glu Thr Ala Met Tyr Val Asn Ser Glu Ser Val Lys Lys Val Ile
165 170 175

Pro Tyr Ile Asp Leu Ala Met Ile Asp Ile Lys Ser Met Asn Asp Glu
180 185 190

```
Ile His Arg Lys Phe Thr Gly Val Ser Asn Glu Ile Ile Leu Gln Asn
        195                 200                 205

Ile Lys Leu Ser Asp Glu Leu Ala Lys Glu Ile Ile Ile Arg Ile Pro
    210                 215                 220

Val Ile Glu Gly Phe Asn Ala Asp Leu Gln Ser Ile Gly Ala Ile Ala
225                 230                 235                 240

Gln Phe Ser Lys Ser Leu Thr Asn Leu Lys Arg Ile Asp Leu Leu Pro
                245                 250                 255

Tyr His Asn Tyr Gly Glu Asn Lys Tyr Gln Ala Ile Gly Arg Glu Tyr
            260                 265                 270

Ser Leu Lys Glu Leu Lys Ser Pro Ser Lys Asp Lys Met Glu Arg Leu
        275                 280                 285

Lys Ala Leu Val Glu Ile Met Gly Ile Pro Cys Thr Ile Gly Ala Glu
    290                 295                 300


<210> SEQ ID NO 8
<211> LENGTH: 385
<212> TYPE: PRT
<213> ORGANISM: Clostridium butyricum

<400> SEQUENCE: 8

Met Arg Met Tyr Asp Tyr Leu Val Pro Ser Val Asn Phe Met Gly Ala
 1               5                  10                  15

Asn Ser Val Ser Val Val Gly Glu Arg Cys Lys Ile Leu Gly Gly Lys
            20                  25                  30

Lys Ala Leu Ile Val Thr Asp Lys Phe Leu Lys Asp Met Glu Gly Gly
        35                  40                  45

Ala Val Glu Leu Thr Val Lys Tyr Leu Lys Glu Ala Gly Leu Asp Val
    50                  55                  60

Val Tyr Tyr Asp Gly Val Glu Pro Asn Pro Lys Asp Val Asn Val Ile
65                  70                  75                  80

Glu Gly Leu Lys Ile Phe Lys Glu Glu Asn Cys Asp Met Ile Val Thr
                85                  90                  95

Val Gly Gly Gly Ser Ser His Asp Cys Gly Lys Gly Ile Gly Ile Ala
            100                 105                 110

Ala Thr His Glu Gly Asp Leu Tyr Asp Tyr Ala Gly Ile Glu Thr Leu
        115                 120                 125

Val Asn Pro Leu Pro Pro Ile Val Ala Val Asn Thr Thr Ala Gly Thr
    130                 135                 140

Ala Ser Glu Leu Thr Arg His Cys Val Leu Thr Asn Thr Lys Lys Lys
145                 150                 155                 160

Ile Lys Phe Val Ile Val Ser Trp Arg Asn Leu Pro Leu Val Ser Ile
                165                 170                 175

Asn Asp Pro Met Leu Met Val Lys Lys Pro Ala Gly Leu Thr Ala Ala
            180                 185                 190

Thr Gly Met Asp Ala Leu Thr His Ala Ile Glu Ala Tyr Val Ser Lys
        195                 200                 205

Asp Ala Asn Pro Val Thr Asp Ala Ser Ala Ile Gln Ala Ile Lys Leu
    210                 215                 220

Ile Ser Gln Asn Leu Arg Gln Ala Val Ala Leu Gly Glu Asn Leu Glu
225                 230                 235                 240

Ala Arg Glu Asn Met Ala Tyr Ala Ser Leu Leu Ala Gly Met Ala Phe
                245                 250                 255

Asn Asn Ala Asn Leu Gly Tyr Val His Ala Met Ala His Gln Leu Gly
```

-continued

```
            260                 265                 270

Gly Leu Tyr Asp Met Ala His Gly Val Ala Asn Ala Met Leu Leu Pro
        275                 280                 285

His Val Glu Arg Tyr Asn Met Leu Ser Asn Pro Lys Lys Phe Ala Asp
    290                 295                 300

Ile Ala Glu Phe Met Gly Glu Asn Ile Ser Gly Leu Ser Val Met Glu
305                 310                 315                 320

Ala Ala Glu Lys Ala Ile Asn Ala Met Phe Arg Leu Ser Glu Asp Val
                325                 330                 335

Gly Ile Pro Lys Ser Leu Lys Glu Met Gly Val Lys Gln Glu Asp Phe
            340                 345                 350

Glu His Met Ala Glu Leu Ala Leu Leu Asp Gly Asn Ala Phe Ser Asn
        355                 360                 365

Pro Arg Lys Gly Asn Ala Lys Asp Ile Ile Asn Ile Phe Lys Ala Ala
    370                 375                 380

Tyr
385


<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 9

cgcggatccg tgattggagg agtaaaaatg ataag                              35


<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 10

tcccccgggg gaatccttta aatagtatta attaataagc                         40


<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 11

gttacccggg gctcctgcag ctcgactttt taac                               34


<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 12

tttcacccgg gaaacagcta tgaccatgat tacg                               34
```

-continued

```
<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 13

ttggatccag tatctataaa tgatccaatg c                                 31


<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 14

ttagatcttt taaatagtat taattaataa gcagcc                            36
```

DIMERIC GLYCEROL DEHYDRATASES

This application is a divisional of application Ser. No. 11/839,455 filed Aug. 15, 2007 now U.S. Pat. No. 7,695,943, which is a divisional of application Ser. No. 10/043,639 filed Jan. 9, 2002, now U.S. Pat. No. 7,267,972, which is a continuation of International Application No. PCT/FR00/01981, filed Jul. 7, 2000, which claims priority to French Application No. 99/08939, filed Jul. 9, 1999. The entire contents of each of the above-referenced disclosures are specifically incorporated herein by reference.

This invention relates to a process for the preparation of 1,3-propanediol from a carbon-containing substance, said process comprising a step involving the culture of a recombinant micro-organism not producing coenzyme B12 in the absence of the addition of coenzyme B12 or of one of its precursors.

The invention also relates to a nucleic acid coding for a glycerol dehydratase, the catalytic activity of which is independent of the presence of coenzyme B12 or of one of its precursors as well as a nucleic acid coding for a 1,3-propanol dehydrogenase implicated in the synthesis of 1,3-propanediol.

The invention also relates to recombinant vectors and host cells comprising said nucleic acids as well as the polypeptides encoded by the latter.

1,3-Propanediol is a substance of great industrial importance, used mainly in the industrial production of detergents and polymers.

Thus, 1,3-propanediol is used in liquid detergents as a stabilizing agent for lipases, amylases and proteases as well as "protective softener" in the liquid detergents for dishwashing by hand.

Moreover, 1,3-propanediol is used increasingly in the industrial production of polymers, more particularly as a monomer used to synthesize polyesters, polyethers or polyurethanes.

Currently, the production of 1,3-propanediol is achieved mainly by chemical synthesis involving hydration (in acid medium) of acrolein to 3-hydroxypropionaldehyde, which is then reduced to 1,3-propanediol by catalytic hydrogenation.

Such a process is expensive and makes use of a toxic product, acrolein. Furthermore, this synthesis is poorly selective and generates a large number of unusable by-products.

Another synthetic route consists of hydrocarbonylation of ethylene oxide by carbon monoxide and hydrogen under high pressure in the presence of catalysts and solvents.

Such a reaction produces a dioxane which is then hydrogenated to 1,3-propanediol. This second process of chemical synthesis is also very expensive.

For several years an alternative to the production of 1,3-propanediol by chemical synthesis has been the subject of various studies: the bioconversion of glycerol to 1,3-propanediol by certain bacterial strains such as *Citrobacter, Clostridium, Enterobacter, Klebsiella, Lactobacillus* and *Pelobacter.*

In particular, the conversion of glycerol to 1,3-propanediol in facultative anaerobic bacteria such as bacteria of the *Klebsiella* genus, *Citrobacter* genus or even *Enterobacter agglomerans* has been studied.

Thus, attempts have been made to clone the genes coding for enzymes responsible for the conversion of glycerol to 1,3-propanediol from the bacterium *Klebsiella pneumoniae.*

More particularly, the cloning of the genes coding for two enzymes has been investigated, a glycerol dehydratase which catalyses the conversion of glycerol to 3-hydroxypropionaldehyde and a 1,3-propanediol dehydrogenase which catalyses the conversion of 3-hydroxypropionaldehyde to 1,3-propanediol, respectively.

U.S. Pat. Nos. 5,633,362 and 5,821,092 describe the cloning of a genomic fragment of about 35 kb of the bacterium *Klebsiella pneumoniae*, said DNA fragment containing a sequence coding for an active diol dehydratase. Such a genomic fragment was obtained by screening of several cosmid libraries of the bacterial species *Klebsiella pneumoniae* and *Klebsiella aerogenes.*

It is described in these patents that strains of *E. coli* DH5α were transformed with these cosmids and the bacterial transformants were screened for their capacity to convert glycerol into 1,3-propanediol. A low level of production of 1,3-propanediol was observed in certain clones of bacterial transformants. This led to the deduction that the diol dehydratase encoded by the cosmids selected might be responsible for the conversion of glycerol to 1,3-propanediol observed.

Nonetheless, the production of 1,3-propanediol by the *E. coli* DH5α strains transformed by the cosmids selected necessarily required the presence in the bacterial culture medium of vitamin B12 or one of its precursors.

Furthermore, the fermentation time necessary for the detection of 1,3-propanediol production was very long (from 78 to 132 hours) and the level of production of 1,3-propanediol was very low.

U.S. Pat. No. 5,686,276 in the name of DU PONT DE NEMOURS & COMPANY describes a process making possible the bioconversion of D-glucose to 1,3-propanediol by an *E. coli* strain transformed by the cosmid DNA originating from *Klebsiella pneumoniae*. Again, the production of 1,3-propanediol requires the use of culture medias adapted to the *E. coli* cells transformed by a *Klebsiella pneumoniae* cosmid containing vitamin B12, for example at a concentration of 800 μg/ml.

The levels of production of 1,3-propanediol observed were very low, of the order of 0.5 g/l to 10 g/l.

The presence of vitamin B12 in the culture medium of the cells transformed by the *Klebsiella pneumoniae* DNA of the U.S. patents cited above is necessary owing to the fact that the co-enzyme B12 is a necessary cofactor for the catalytic activity of the glycerol dehydratase of *Klebsiella pneumoniae.*

The coenzyme B12 or any of its precursors such as vitamin B12 is an extremely expensive and very unstable substance, and this makes it difficult and even impossible to transfer to an industrial scale the processes for the conversion of glucose or glycerol to 1,3-propanediol by bacterial fermentation with the aid of such strains.

In addition, coenzyme B12 and its precursors pass through the membranes of certain micro-organisms, such as yeasts, with difficulty, and this requires the presence of very high concentrations of these substances in the culture medium in order that they become accessible to the intracellular enzymes of which coenzyme B12 is the cofactor.

Moreover, an alternative which would consist of introducing the DNA coding for the known glycerol dehydratases implicated in the conversion of glycerol to 1,3-propanediol into bacteria synthesizing vitamin B12 encounters considerable technical obstacles.

In fact, only certain bacterial species synthesize vitamin B12 naturally, such as the *Pseudomonas* bacteria or also the propionibacteria, the genetics of which is very poorly understood and which are therefore not capable of undergoing genetic modifications.

Other bacteria which synthesize vitamin B12 naturally and the genetics of which is well understood such as *Klebsiella*

*pneumoniae* present considerable problems of toxicity which makes them unsuitable for industrial use.

In addition to this first disadvantage it was possible to obtain only a low level of production of 1,3-propanediol after transformation of *Klebsiella pneumoniae*. Thus, the PCT application No. WO 98/21 339 describes recombinant *Klebsiella pneumoniae* expressing both the genes for the metabolism of glucose to glycerol and the genes for the metabolism of glycerol to 1,3-propanediol. The level of production of 1,3-propanediol observed starting from glucose was low, of the order of 10 g per liter.

The technical obstacles to the development of a process for the bioconversion of a carbon-containing substance to 1,3-propanediol mentioned above have been overcome by the invention.

In fact, the applicant has isolated and characterized a nucleic acid which codes for a glycerol dehydratase, the catalytic activity of which is independent of the presence of coenzyme B12 or any one of these precursors.

The genes coding for the coenzyme B12-independent glycerol dehydratase were isolated by the applicant from the genome of the bacterium *Clostridium butyricum* VPI 1718. They code for a dimeric protein constituted of two protein subunits, the polypeptides ORF11 and ORF12, respectively.

It has been shown according to the invention that the sequences coding for the polypeptides ORF11 and ORF12 are located in a unique operon in the *Clostridium butyricum* genome, said operon also comprising downstream from the nucleic acid sequence coding for the ORF12 subunit a region coding for a 1,3-propanediol dehydrogenase.

The operon according to the invention comprises from the 5' end to the 3' end a promoter of transcription, the sequence orf11 coding for ORF11, the first subunit of the coenzyme B12-independent glycerol dehydratase, the sequence orf12, coding for ORF12 the second subunit of the glycerol dehydratase and a sequence dhaT coding for a novel 1,3-propanediol dehydrogenase (DHAT).

Thus, the nucleic acid sequences coding for the two protein subunits of the glycerol dehydratase and for 1,3-propanediol dehydrogenase form part of a unique operon, the three coding sequences being regulated by a unique promoter sequence situated on the 5' side of the sequence coding for the subunit ORF11.

It has also been shown according to the invention that the transformation of a bacterial cell host by a sequence comprising the regions coding respectively for ORF11, ORF12 and DHAT was such as to provide on the transformed cell host the capacity to produce 1,3-propanediol from glucose or glycerol in the absence of the coenzyme B12 or any of its precursors when these sequences are placed under the control of a suitable promoter that is functional in the cell host in which the expression of these sequences is desired.

The applicant has also shown that the transformation of a bacterial cell host producing 1,3-propanediol naturally by the sequences coding for the two subunits of the glycerol dehydratase according to the invention was such as to induce a significant increase in the production of propanediol in the recombinant bacterial hosts obtained.

The object of the invention is thus a process for the preparation of 1,3-propanediol from a carbon-containing substance, said process comprising at least one step which consists of culturing a recombinant micro-organism in which has been integrated at least one nucleic acid coding for the two subunits of a glycerol dehydratase the catalytic activity of which is independent of the presence of coenzyme B12 or one of its precursors.

Advantageously, the glycerol dehydratase whose catalytic activity is independent of the presence of coenzyme B12 is derived from the bacterium *Clostridium butyricum.*

Preferably, the coenzyme B12-independent glycerol dehydratase is a dimeric protein composed of a first polypeptide having at least 50% amino acid identity with the polypeptide of sequence SEQ ID No. 6 and a second polypeptide having at least 50% amino acid identity with the polypeptide of sequence SEQ ID No. 7. Very advantageously, the coenzyme B12-independent glycerol dehydratase is composed of a first and second polypeptide having an amino acid identity of at least 60%, 65%, 70%, 80%, 85%, 90%, 95% or even 99% with the polypeptide of sequence SEQ ID No. 6 and the polypeptide of sequence SEQ ID No. 7, respectively.

The "identity percentage" of nucleotides or amino acids between two sequences in the sense of the present invention can be determined by comparing two optimally aligned sequences, through a window of comparison.

The part of the nucleotide or peptide sequence in the window of comparison may thus include additions or deletions (for example, "gaps") with respect to the reference sequence (which does not comprise these additions or these deletions) so as to obtain an optimal alignment of the two sequences.

The percentage of identity is calculated by determining the number of positions at which an identical nucleotide base or amino acid is observed in the two sequences compared, then by dividing the number of positions at which there is identity between the two bases or the two amino acids by the total number of positions in the window of comparison, then by multiplying the result by a hundred in order to obtain the percentage of sequence identity.

The optimal alignment of the sequences for the comparison can be carried out by computer with the aid of known algorithms (for example, the FASTA software of the company WISCONSIN GENETICS SOFTWARE PACKAGE, GENETICS COMPUTER GROUP (GCG), 575 Science Doctor, Madison, Wis.).

As an illustration, the percentage of sequence identity can be calculated with the aid of the previously mentioned FASTA software, by using exclusively the default parameters.

Very preferably, the percentage of nucleotide or amino acid identity between two nucleic acid or amino acid sequences is calculated with the aid of the BLAST software (version 2.06 of September 1998) by using exclusively the default parameters.

The differences in amino acids that a polypeptide according to the invention may comprise with respect to the reference amino acid sequence, such as defined in the listing of sequences presented at the end of the present description, may or may not result in substitutions, deletions or additions of one or more consecutive amino acids.

In accordance with another aspect of the process according to the invention, the recombinant micro-organism comprises in addition a nucleic acid coding for a 1,3-propanediol dehydrogenase, preferably a 1,3-propanediol dehydrogenase of *Clostridium butyricum.*

Preferably, the 1,3-propanediol dehydrogenase is a polypeptide having at least 90% amino acid identity with the polypeptide of sequence SEQ ID No. 8.

Very advantageously, the invention also relates to a polypeptide having at least 95%, 97%, 98% or 99% amino acid identity with the polypeptide of sequence SEQ ID No. 8.

An essential characteristic of the process according to the invention is that the step involving the culture of the recombinant micro-organism is carried out in the absence of coenzyme B12 or one of its precursors.

In accordance with another aspect, the process is also characterized in that the carbon-containing source is selected from the carbohydrates and the polyols.

The carbohydrate may, for example, be glucose.

The polyol may, for example, be glycerol.

Preferably, the process according to the invention is carried out with a micro-organism selected from the micro-organisms not naturally producing coenzyme B12 or one of its precursors.

Such a micro-organism may be a bacterium belonging to the *Clostridium* or *Escherichia* genus.

It may also be a yeast of the *Saccharomyces cerevisiae* species.

In accordance with a particular embodiment, the process is also characterized in that the recombinant micro-organism also comprises nucleic acids coding respectively for a glycerol-3-phosphate dehydrogenase and a glycerol-3-phosphatase, in which case the recombinant micro-organism is capable of converting a carbon-containing source such as glucose into 1,3-propanediol in high yield.

Another object of the invention is a nucleic acid comprising all or part of a polynucleotide coding for at least one subunit of a glycerol dehydratase whose catalytic activity is independent of the presence of coenzyme B12 or one of its precursors.

Preferably, a nucleic acid according to the invention is available in a purified or isolated form.

Such a polynucleotide should have preferably at least 50% nucleotide identity with the polynucleotide of sequences SEQ ID No. 1 or SEQ ID No. 2.

A polynucleotide with a sequence complementary to the polynucleotides of sequences SEQ ID No. 1 or SEQ ID No. 2 also constitutes an object of the invention.

Also included in the invention are nucleic acids comprising all or part of a polynucleotide possessing at least 60%, 65%, 70%, 75%, 85%, 90%, 95%, 98%, 99%, 99.5% or even 99.8% of nucleotide identity with the nucleotide sequence of any one of the nucleic acids whose sequences are defined in the present description, or a nucleic acid with a complementary sequence.

The term "isolated" in the sense of the present invention designates biological material which has been removed from its original environment (the environment in which it is naturally located).

For example, a polynucleotide present in the natural state in a plant or an animal is not isolated.

The same polynucleotide separated from the adjacent nucleic acids within which it is naturally inserted in the genome of the plant or the animal is isolated.

Such a polynucleotide may be included in a vector and/or such a polynucleotide may be included in a composition and remain nonetheless in the isolated state owing to the fact that the vector or the composition does not constitute its natural environment.

The term "purified" does not require that the material be present in an absolutely pure form, exclusive of the presence of other substances. It is rather a relative definition.

A polynucleotide is in the purified state after purification from the starting material or from the natural material by at least one order of magnitude, preferably two or three orders of magnitude and even more preferably four or five orders of magnitude.

For the purposes of the present description the expression "nucleotide sequence" can be used to designate indiscriminately a polynucleotide or a nucleic acid. The expression "nucleotide sequence" includes the genetic material itself and is hence not limited to information concerning its sequence.

The invention also relates to a nucleic acid coding for the two protein subunits of the coenzyme B12-independent glycerol dehydratase of *Clostridium butyricum.*

Preferably, such a nucleic acid is characterized in that it comprises a first polynucleotide having at least 50% nucleotide identity with the polynucleotide of sequence SEQ ID No. 1 and a second polynucleotide having at least 50% nucleotide identity with the polynucleotide of sequence SEQ ID No. 2.

According to a particular embodiment, such a nucleic acid coding for the two protein subunits of the coenzyme B12-independent glycerol dehydratase should comprise in addition a sequence with a promoter function, functional in the host cell in which the expression of the polynucleotides coding for the two subunits of this enzyme is desired.

Such a transcription promoter nucleotide sequence may be the promoter sequence SEQ ID No. 3 or a sequence having at least 80% nucleotide identity with this latter.

Another object of the invention is a nucleic acid with a bacterial promoter function, in particular in *Clostridium butyricum*, comprising a polynucleotide having at least 80% nucleotide identity with the sequence SEQ ID No. 3, or a polynucleotide with a complementary sequence.

As already mentioned above, organization in a unique operon makes possible, in the bacterium *Clostridium butyricum*, the synthesis of a transcription product (messenger RNA) comprising both the sequences coding for the two protein subunits of the coenzyme B12-independent glycerol dehydratase, which catalyses the conversion of glycerol to 3-hydroxypropionaldehyde (3-HPA) and the 1,3-propanediol dehydrogenase (DHAT) which catalyses the conversion of 3-HPA to 1,3-propanediol.

The invention thus also relates to a nucleic acid comprising all or part of a polynucleotide coding for a 1,3-propanediol dehydrogenase having at least 90% nucleotide identity with the polynucleotide of sequence SEQ ID No. 4, or a complementary polynucleotide sequence.

In a particular embodiment of a purified or isolated nucleic acid according to the invention, it may be advantageous to be able to include in the same sequence the nucleic acids coding respectively for the two protein subunits of the glycerol dehydrogenase and for the 1,3-propanediol dehydrogenase, such a nucleic acid coding then for the two enzymes capable of catalysing all of the bioconversion steps from glycerol to 1,3-propanediol.

Consequently, the invention also relates to a nucleic acid comprising from the 5' end to the 3' end:

a) a first nucleic acid characterized in that it comprises a first polynucleotide having at least 50% nucleotide identity with the polynucleotide of sequence SEQ ID No. 1 and a second polynucleotide having at least 50% nucleotide identity with the polynucleotide of sequence SEQ ID No. 2;

b) a second nucleic acid comprising a polynucleotide coding for a 1,3-propanediol dehydrogenase having at least 90% nucleotide identity with the polynucleotide of sequence SEQ ID No. 4.

The nucleotide sequences coding respectively for the glycerol dehydratase and the 1,3-propanediol dehydrogenase of the nucleic acid described above can in addition also be advantageously placed under the control of a suitable promoter sequence, such as the sequence SEQ ID No. 3 or any other promoter sequence functional in the host cell in which their expression is desired.

A nucleic acid complying with the above definition is for example the polynucleotide of sequence SEQ ID No. 5 or also a polynucleotide having at least 50% nucleotide identity with the polynucleotide sequence SEQ ID No. 5.

The nucleic acid sequence SEQ ID No. 5 comprises the following characteristic functional elements:

a) a transcription terminator for the coding region located upstream from the 1,3-propanediol operon in the *Clostridium butyricum* genome.

This transcription terminator motif possesses a hairpin structure centred on the nucleotide at position 27 of the sequence SEQ ID No. 5 (ΔG=−25.2 kcal/mol) which comprises a 19 by stem, the two strands of the stem being constituted respectively by the nucleotides in positions 5 to 23 and nucleotides in positions 30 to 48 of the sequence SEQ ID No. 5, the loop of the hairpin structure being constituted by the nucleotides in positions 24 to 29 of the sequence SEQ ID No. 5.

This transcription terminator motif is followed by the sequence ATTTT.

b) Promoter of the 1,3-propanediol operon.

The promoter of the 1,3-propanediol operon is located between the nucleotide at position 100 and the nucleotide at position 200 of the sequence SEQ ID No. 5.

This promoter comprises a TAGATA box sequence (−35) located between the nucleotide at position 142 and the nucleotide at position 147 of the sequence SEQ ID No. 5. This promoter also comprises a TATTAT box sequence (−10) located between the nucleotide at position 164 to the nucleotide at position 169 of the sequence SEQ ID No. 5, the distance between the −35 boxes and the −10 boxes being 16 bp.

c) orf11 (sequence coding for the first subunit of the glycerol dehydrogenase).

It is a unique open reading frame of 2,361 by coding for the ORF11 polypeptide of 787 amino acids of sequence SEQ ID No. 6.

The initiation codon ATG is located between the nucleotide at position 313 and the nucleotide at position 315 of the sequence SEQ ID No. 5. The open reading frame is terminated by a stop codon with the sequence TAA located between the nucleotide at position 2674 and the nucleotide at position 2676 of the sequence SEQ ID No. 5.

In addition, a ribosomal binding site with the sequence GAGGAG precedes the initiation codon and is located between the nucleotide at position 302 and the nucleotide at position 307 of the sequence SEQ ID No. 5.

d) orf12 (sequence coding for the second subunit of the glycerol dehydrogenase). It is a unique open reading frame of 912 by coding for a polypeptide of 304 amino acids of sequence SEQ ID No. 7. The initiation codon with the sequence ATG is located between the nucleotide at position 2704 and the nucleotide at position 2706 of the sequence SEQ ID No. 5. The open reading frame is terminated by a stop codon with the sequence TAA located between the nucleotide at position 3616 and the nucleotide at position 3618 of the sequence SEQ ID No. 5.

In addition, a ribosomal binding site with the sequence AAGGGGA precedes the initiation codon and is located between the nucleotide at position 2689 and the nucleotide at position 2695 of the sequence SEQ ID No. 5.

e) dhat (sequence coding for 1,3-propanediol dehydrogenase)

It is a unique open reading frame of 1155 by coding for a polypeptide of 385 amino acids of the sequence SEQ ID No. 8.

The initiation codon with the sequence ATG is located between the nucleotide at position 3678 and the nucleotide at position 3680 of the sequence SEQ ID No. 5.

The open reading frame is terminated by a stop codon with the sequence TAA located between the nucleotide at position 4833 and the nucleotide at position 4835 of the sequence SEQ ID No. 5.

In addition, a ribosomal binding site with the sequence AGGAGA precedes the initiation codon and is located between the nucleotide at position 3663 and the nucleotide at position 3668 of the sequence SEQ ID No. 5.

f) Transcription terminator of the 1,3-propanediol operon.

The transcription terminator of the 1,3-propanediol operon possesses a hairpin structure centred on the nucleotide at position 4933 of the sequence SEQ ID No. 5 (ΔG=−27.4 kcal/mol) and comprises a stem of 22 by constituted respectively by the nucleotides located at positions 4909 to 4930 of the sequence SEQ ID No. 5 and the nucleotides located at positions 4936 to 4957 of the sequence SEQ ID No. 5.

The loop of the hairpin is constituted by the sequence extending from the nucleotide at position 4931 to the nucleotide at position 4935 of the sequence SEQ ID No. 5.

The hairpin structure is followed by the sequence TATTTAATT.

Each of the functional sequences comprised in the 1,3-propanediol operon of sequence SEQ ID No. 5 such as described above may be employed individually, for example by insertion in a cloning and/or expression vector irrespective of whether it is one of the regions coding for a polypeptide of the invention or a regulatory region (transcription promoter or terminator).

These nucleotide sequences of interest can also be obtained according to the procedures well-known to the man skilled in the art such as the use of restriction enzymes, the use of which is described in detail in the monograph by SAMBROOK et al. (1989) or also by selective amplification of the target sequence of interest, for example by PCR.

Also included in the invention are the nucleic acids hybridizing under hybridization conditions of high stringency with a nucleic acid selected from the nucleotide sequences SEQ ID No. 1 to SEQ ID No. 5.

By "hybridization conditions of high stringency" in the sense of the present invention is meant the following hybridization conditions:

- prehybridization of the filters for 8 hours at 65° C. in a buffer composed of 6×SSC, 50 mM Tris-HCl (pH 7.5), 1 mM EDTA, 0.02% PVP, 0.02% FICOLL, 0.02% SAB and 500 μg/ml of denatured salmon sperm DNA;
- hybridization of the filters for 48 hours at 65° C. in the presence of 1×SSC buffer corresponding to 0.15 M of NaCl and 0.05 M of sodium citrate;
- three washes of the filter in a solution containing 2×SSC buffer and 0.1% SDS at 68° C. for 15'.

The high stringency conditions defined above are adapted to the hybridization of a nucleic acid molecule 20 nucleotides long.

It is obvious that these hybridization conditions must be adapted as a function of the length of the nucleic acid whose hybridization is required, in accordance with procedures well-known to the man skilled in the art.

The conditions suitable for hybridization may for example be adapted according to the teaching contained in the monograph of HAMES & HIGGINS (1985) or also in the monograph of SAMBROOK et al.; (1989).

Also included in the invention are the nucleic acids comprising at least 20 consecutive nucleotides of a polynucleotide selected from the nucleotide sequences SEQ ID No. 1 to SEQ ID No. 5.

Such nucleic acids advantageously comprise 20, 25, 30, 35, 40, 50, 100, 150, 200 to 250, 300, 400, 500 consecutive nucleotides of a polynucleotide selected from the nucleotide sequences SEQ ID No. 1 to SEQ ID No. 5.

Such nucleic acids may comprise 20, 25, 30, 35, 40, 50, 100, 150, 200, 250, 300, 400 or 500 consecutive nucleotides of a polynucleotide selected from the nucleotide sequences SEQ ID No. 1 to SEQ ID No. 5.

Such nucleic acids may in particular be useful as nucleotide probes or primers in order to detect the presence of any one of the nucleotide sequences of SEQ ID No. 1 to SEQ ID No. 5 in a sample.

Such nucleotide probes or primers can be used in particular in order to measure the expression of any one of the transcription products of the coding regions orf11, orf12 or dhat in accordance with the procedures well-known to the man skilled in the art.

In order to improve still further the capacity of the host cells transformed with a nucleic acid according to the invention to produce 1,3-propanediol from glucose, such a recombinant cell host can also be transformed with one or more genes coding for one or more enzymes capable of catalysing the transformation of glucose to glycerol.

An enzyme couple capable of carrying out the conversion of glucose to glycerol is for example a glycerol-3-phosphate dehydrogenase and a glycerol-3-phosphatase.

Thus, a nucleic acid according to the invention will comprise, in addition to the sequences coding for the coenzyme B12-independent glycerol dehydratase and the 1,3-propanediol dehydrogenase (dhaT), a third nucleic acid coding for a glycerol-3-phosphate dehydrogenase and a fourth nucleic acid coding for a glycerol-3-phosphatase.

In particular, it will be possible to use a nucleic acid coding for gpd1 glycerol-3-phosphate dehydrogenase and a fourth nucleic acid coding for gpp2 glycerol-3-phosphatase.

Gpd1 is described for example by LARSSON et al. (1993) Mol. Microbiol., 10, 1101-1111.

Gpd2 is described for example by HIRAYAMA et al. (1995). Mol. Gen. Genet., 249, 127-138.

In accordance with yet another aspect, the invention relates to a recombinant cloning and/or expression vector comprising a nucleic acid coding for a coenzyme B12-independent glycerol dehydratase or a 1,3-propanediol dehydrogenase according to the invention.

Such a recombinant vector will advantageously comprise a constitutive or inducible promoter sequence capable of directing the expression of the coenzyme B12-independent glycerol dehydratase and/or a 1,3-propanediol dehydrogenase and a Rho-independent transcription terminator.

It may, for example, be a shuttle vector capable of replicating in different cell hosts.

A first preferred recombinant vector according to the invention is the plasmid pSPD5 contained in the *Escherichia coli* strain filed at the National Collection of Cultures of Micro-organisms (NCCM) on 24 Jun. 1999 under the access No. 1-2243.

Other preferred vectors according to the invention are, for example, the following:

- the vectors pTPG(−) and pOPG represented in FIGS. 3 and 4.
- the vectors pSGD and pPPF2 represented in FIGS. 5 and 6;
- vectors possessing the replicon of pCB101, such as the vector pCTC511 (WILLIAMS et al., 1990) or also the vector pSYSL2 (LEE et al., 1992)
- a shuttle vector carrying the replicon pAMβ1 of *Enterococcus faecalis* DS-5, such as the vector pCTC41 (WILLIAMS et al., 1990);
- the *E. coli B. subtilis/C. acetobutylicum* shuttle vectors designated pKNT11 and pKNT14 (TRUFFAUT et al., 1989);

The invention also relates to a recombinant host cell comprising a nucleic acid or recombinant vector according to the invention.

Such a recombinant host cell advantageously comprise a nucleic acid coding for the coenzyme B12-independent glycerol dehydratase or also a vector containing such a nucleic acid.

Preferably, such a recombinant host cell should comprise a nucleic acid coding both for the two protein subunits of the coenzyme B12-independent glycerol dehydratase as well as for the DHAT.

It may be, indiscriminately, a bacterium, a fungus or a yeast.

A recombinant bacterial host cell will be preferably selected from *Escherichia coli, Clostridium* or also *Bacillus, Lactobacillus* and *Lactococcus.*

A recombinant yeast cell according to the invention will preferably be the *Saccharomyces cerevisiae* strain.

A preferred recombinant host cell according to the invention is the *Escherichia coli* strain filed at the National Collection of Cultures of Micro-organisms (NCCM) on 24 Jun. 1999 under the access No. I-2243.

The object of the invention also includes the polypeptides constituting respectively each of the two protein subunits constituting the dimeric coenzyme B12-independent glycerol dehydratase according to the invention.

Preferably, a polypeptide according to the invention is available in an isolated or purified form.

The invention also relates to a polypeptide constituting the enzyme 1,3-propanediol dehydrogenase of *Clostridium butyricum.*

More particularly, the invention relates to a polypeptide comprising all or part of an amino acid sequence having at least 50% amino acid identity with the sequence SEQ ID No. 6 or SEQ ID No. 7.

The invention also relates to a dimeric protein composed of a first polypeptide having at least 50% amino acid identity with the polypeptide of sequence SEQ ID No. 6 and a second polypeptide having at least 50% amino acid identity with the polypeptide of sequence SEQ ID No. 7.

In a much preferred manner, such a polypeptide exhibits a glycerol dehydratase catalytic activity not requiring the presence of coenzyme B12, such a catalytic activity being capable of being measured in conformity with the examples.

Another object of the invention consists of a polypeptide comprising all or part of an amino acid sequence having at least 80% amino acid identity with the sequence SEQ ID No. 8.

In a very preferred manner, such a polypeptide exhibits a catalytic activity of 1,3-propanediol dehydrogenase.

The invention also relates to a process for the production of a polypeptide according to the invention, characterized in that it comprises the following steps:

a) preparation of a recombinant expression vector according to the invention;

b) introduction of the recombinant expression vector of step a) into a suitable host cell;

c) culture of the recombinant host cell of step b) in a suitable culture medium;

d) recovery of the recombinant polypeptide produced from the culture supernatant or from the cell lysate;

e) if necessary, purification of the polypeptide recovered.

The polypeptides according to the invention can be purified for example by passage through a nickel or copper ion affinity chromatography column.

These polypeptides can be characterized in addition by their glycerol dehydratase or 1,3-propanediol dehydrogenase enzymatic activity, as indicated in the examples.

The polypeptides according to the invention can also be purified for example by high performance liquid chromatography such as reverse phase and/or cation exchange HPLC chromatographies.

Also included in the invention are the polypeptides comprising amino acid modifications ranging from 1, 2, 3, 4, 5, 10 to 20 substitutions, additions or deletions of an amino acid with respect to the sequence of one or other of the two protein subunits of the coenzyme B12-independent glycerol dehydrogenase or of the 1,3-propanediol dehydrogenase.

In a very preferred manner, the amino acid modifications in the polypeptide of the invention relative to the reference polypeptides should not induce a significant change in their biological activity. Thus, the modifications in the amino acid sequence of the protein subunits of the coenzyme B12-independent glycerol dehydratase according to the invention should be such that the catalytic activity will be at least equal to 50% of the initial catalytic activity and will preferably be an improvement on the initial catalytic activity.

The same holds for the amino acid modifications in the protein sequence of the 1,3-propanediol dehydrogenase according to the invention.

Any one of the polypeptide according to the invention or even a peptide fragment of the latter can be used for the preparation of antibodies directed specifically against this latter.

An object of the invention is also constituted by a polypeptide comprising at least 20 consecutive amino acids of an amino acid sequence selected from the sequences SEQ ID No. 6 to SEQ ID No. 8.

Advantageously, such a polypeptide should comprise 20, 25, 30, 35, 40, 45, 50, 75 to 100, 125, 150 or 200 consecutive amino acids of a polypeptide selected from the sequences SEQ ID No. 6 to SEQ ID No. 8.

Preferably, such a polypeptide should comprise 20, 25, 30, 35, 40, 45, 50, 60, 70, 80, 90, 100, 125, 150, 175, 200, 250 or 300 consecutive amino acids of a polypeptide selected from the amino acid sequences SEQ ID No. 6 to SEQ ID No. 8.

Such specific antibodies can be used in immunodetection assays making it possible to determine the presence of a coenzyme B12-independent glycerol dehydratase or of a 1,3-propanediol dehydrogenase in a sample.

Such an immunodetection assay represents an alternative to the determination of glycerol dehydratase or 1,3-propanediol dehydrogenase activity in a sample suspected of containing these enzymes.

By "antibodies" in the sense of the invention, is meant polyclonal antibodies but also monoclonal antibodies such as those prepared from hybridomas according to the procedure described by KOHLER & MILSTEIN (1975).

Antibodies in the sense of the present invention also include antibody fragments (Fab', F(ab')$_2$ as well as simple chain FV antibody fragments (U.S. Pat. No. 4,946,778; MARTINEAU et al., (1998)) or also humanised antibodies (REINMANN et al., 1997; LEGER et al. 1997).

The invention will in addition be illustrated by the following figures and examples without being limited by them.

MATERIALS AND METHODS

I. Culture of the Strains

1. Strain Used

Figure 1:
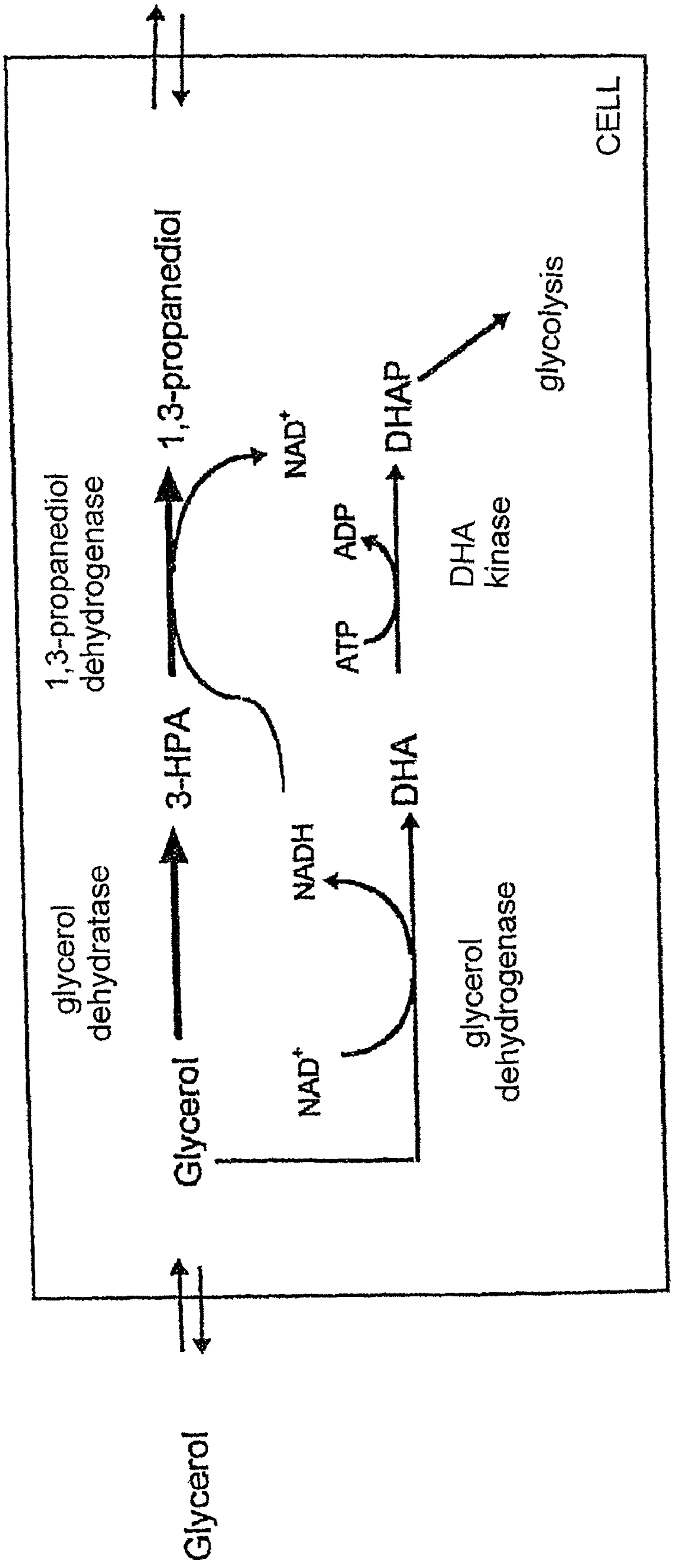
FIG. 1 represents a schema of the metabolic bioconversion route of glycerol to 1,3-propanediol in the bacterium *Clostridium butyricum*.

The *Clostridium butyricum* strain from which the different nucleic acid sequences according to the invention were isolated and characterized is the strain VPI 1718.

The *Clostridium acetobutylicum* strain used for transformation with the different vectors described in the examples is the strain available from the American Type Culture Collection under the No. ATCC 824.

The *Escherichia coli* strain DH5α used for the transfection with the different plasmids described in the examples is the strain available from LIFE TECHNOLOGIES Inc.

2. The Plasmids

The 2.7 kb plasmid pUC18 is described by YANNISCH-PERRON et al. (1985)

The 4.9 kb plasmid pIMPI is described by MERMELSTEIN (1992).

The 7 kb plasmid pSOS95 is described by SOUCAILLE and PAPOUTSAKIS (1996).

3. Culture Media and Culture Conditions

For the culture of the *Escherichia coli* strain the LB medium (described in SAMBROOK et al., 1989) is supplemented with antibiotics (100 μg/ml ampicillin, 300 μg/ml erythromycin and 35 μg/ml chloramphenicol).

The cultures of the *Clostridium* strains, in particular the *Clostridium butyricum* strains or *Clostridium acetobutylicum* DGI strains transformed by the vector pSPD5 were carried out in the following medium, the composition of which is given for 1 liter of culture medium:

| | |
|---|---|
| Yeast extract | 4 g |
| Glycerol | 60 g |
| $KH_2PO_4$ | 0.5 g |
| $K_2HPO_4$ | 0.5 g |
| $MgSO_4$ | 0.2 g |
| $NH_4Cl$ | 1.5 g |
| $FeSO_4$ | 10 mg |
| Biotin | 0.04 mg |
| Para-aminobenzoic acid | 8 mg |

The pH is adjusted to 6 by addition of ammonium and the growth temperature is 37° C.

Clarithromycin is added at a concentration of 40 mg/l for the culture of the *C. acetobutylicum* D61 (pSPP5) strain.

II. Analytical Techniques

1. Determination of the Substrates and Products

All of the substrates (glucose and glycerol) and products (acetate, butyrate, lactate, 1,3-propanediol) are determined by means of high performance liquid chromatography (HPLC).

The HPLC apparatus (pump model 5810, Waters) is equipped with an automatic sample changer (SP 8775, Spectra Physic) having a 20 µl injection loop, an integrator (Intersmat ICR 1B, Shimadzu) and a refractometer (HP 1047A).

The separation is obtained by passage through an ion exclusion column (Aminex R HPX-87H, 300 mm×7.8 mm, Biorad) equipped with a pre-column (Micro-Guard, Biorad) filled with the same ionic resin $H^+$.

The mobile phase is constituted by 0.031 mM sulfuric acid, the flow rate is 0.7 ml/min and the separation is made at room temperature.

2. Determination of Activities a) Determination of 1,3-propanediol Dehydrogenase The determination of 1,3-propanediol dehydrogenase was carried out in a 1 ml volume of the following reaction medium:

| | |
|---|---|
| 1,3-propanediol | 100 mM |
| $NAD^+$ | 2 mM |
| DTT | 2 mM |
| $(NH_4)_2SO_4$ | 30 mM |
| $K_2CO_3$ | 100 mM |

Cell extract: assays on 5 µl, 10 µl, 50 µl
Made up to 1 ml with water

The reduction of $NAD^+$ is monitored by the measurement of the optical density at the wavelength of 340 nanometers.

The extinction coefficient ε (NADH) is 6.22 $mM^{-1}\times cm^{-1}$ b) Determination of Glycerol Dehydratase The determination of glycerol dehydratase is carried out on a cell extract that has previously passed through a desalting column. This determination is carried out in a 1 ml volume of the following reaction medium:

| | |
|---|---|
| KCl | 0.05 M |
| 1,2-propanediol | 0.06 M |
| $KPO_4$ buffer, pH7 | 0.035 M |

Cell extract assay on 5 µl, 10 µl, 20 µl, 30 µl
Made up with water to 1 ml

The reaction is stopped after 10 minutes at 37° C. with the aid of 1 ml of 100 mM citrate buffer, pH 3.6 and 500 µl of 0.1% MBTH.

After 15 minutes at 37° C., 1 ml of water is added and the amount of propionaldehyde formed is determined by measurement of the optical density at the wavelength of 305 nanometers.

The molar extinction coefficient of the product formed is $13.3\times10^3$ $M^{-1}\times cm^{-1}$.

c) Measurement of Biomass

Bacterial growth is monitored by the measurement in aliquot fractions sampled at defined times of the optical density at the wavelength of 620 nanometers for an optical path of 1 cm. It is considered that one optical density unit corresponds to approximately $3\times10^8$ bacteria/ml.

III. Transformation of the Bacteria with the Recombinant Vectors According to the Invention III.1. Transformation of *E. coli* DH5α

The *E. coli* DH5α strain is made competent according to the protocol established by INOUE et al. (1990). This protocol makes it possible to obtain transformation efficiencies of the order of $10^8$ to $10^9$ transformants/mg of pUC18. The cells made competent are then stored at −80° C. The transformation of the competent cells by a plasmid is performed by thermal shock (SAMBROOK et al., 1989).

III.2. Transformation of *C. acetobutylicum*

The plasmid to be introduced into *C. acetobutylicum* (ATCC 824 or DG1) must first be methylated at the Cac8241 sites (=Bsofl). The methylation in vivo is carried out by introducing the plasmid to be methylated in the *E. coli* ER 2275 strain carrying the plasmid pAN1 (which contains the gene coding for the methylase of the phage f3TI of *Bacillus subtilis*). The plasmid DNA preparation used to transform *C. acetobutylicum* must be very pure, purified by ultracentrifugation in a caesium chloride gradient (SAMBROOK et al., 1989) or by using the Qiafilter Plasmid Midiprep kit (QIAGEN).

The transformations are performed in strict anaerobiosis in accordance with the following protocol, adapted from that of MEMMERLSTEIN (1992). The efficiencies are still very low, of the order of $10^2$ transformants per mg of DNA.

From an overnight preculture in CGM medium (10 ml) at 37° C.

Inoculate 50 ml of 2YTG medium with a 10% inoculum

Stop the culture at an O.D.600 of 1.0 to 1.2.

From this point onwards all of the operations are carried out in the anaerobic hood and in ice.

Centrifuge the cells for 10 min at 4 000 g

Wash the cell pellet in 10 ml of electroporation buffer.

Centrifuge for 10 min at 3 000-4 000 g.

Resuspend the cells in 500 ml of electroporation buffer.

The cell suspension is placed in contact with the plasmid (5 to 10 mg of plasmid DNA dissolved in 5 to 50 ml of TE buffer) previously introduced into the electroporation cuvette (0.4 cm thickness). The cuvette and contents are stored in ice.

The mixture is immediately subjected to an electric discharge with the following parameters: V=2500V, C=25 mF and R infinity (BioRad Gene pulser II and Gene controller II). Under these conditions, the time of delivery of the discharge varies from 7 to 12 ms.

The cells are then immediately transferred to 10 ml of 2 YTG medium and incubated at 37° C. until metabolism resumes (formation of bubbles of carbon dioxide and hydrogen).

The culture is then centrifuged and the cell pellet is taken up in a minimal volume of the same medium. The suspension is then spread on RCA medium with an antibiotic.

Composition of the Electroporation Buffer:

| | |
|---|---|
| Sucrose | 270 mM |
| Phosphate buffer ($Na_2HPO_4/NaH_2PO_4$), pH 7.4 | 3 mM |

Example 1

Construction of the Expression Vector pSPD5

The following nucleotide primers were synthesized in order to amplify a nucleotide sequence containing simultaneously orf11, orf12 and dhaT, i.e. all of the sequences coding both for the two protein subunits of the coenzyme B12-independent glycerol dehydratase and the 1,3-propanediol dehydrogenase of *Clostridium butyricum.*

The primer PDH3 (SEQ ID No. 9) includes the BamHI site, the ribosomal binding site and the beginning of orf11.

The primer PDH4 (SEQ ID No. 10) hybridizes with the complementary strand and contains the SmaI site and the end of the dhaT gene.

An amplification reaction with the primers pDH3 and pDH4 was carried out on the genomic DNA of *Clostridium butyricum* under the following conditions:

annealing temperature for the primers: 55° C.;

duration of elongation: 4 minutes;

number of cycles: 15 cycles

The amplification reaction was carried out with the Expand Long Template PCR kit (sold by Boehringer).

This reaction made it possible to amplify a fragment of the expected size of 4.6 kb.

This amplified fragment was purified on agarose gel then digested by the enzymes BamHI and SmaI.

Figure 2:
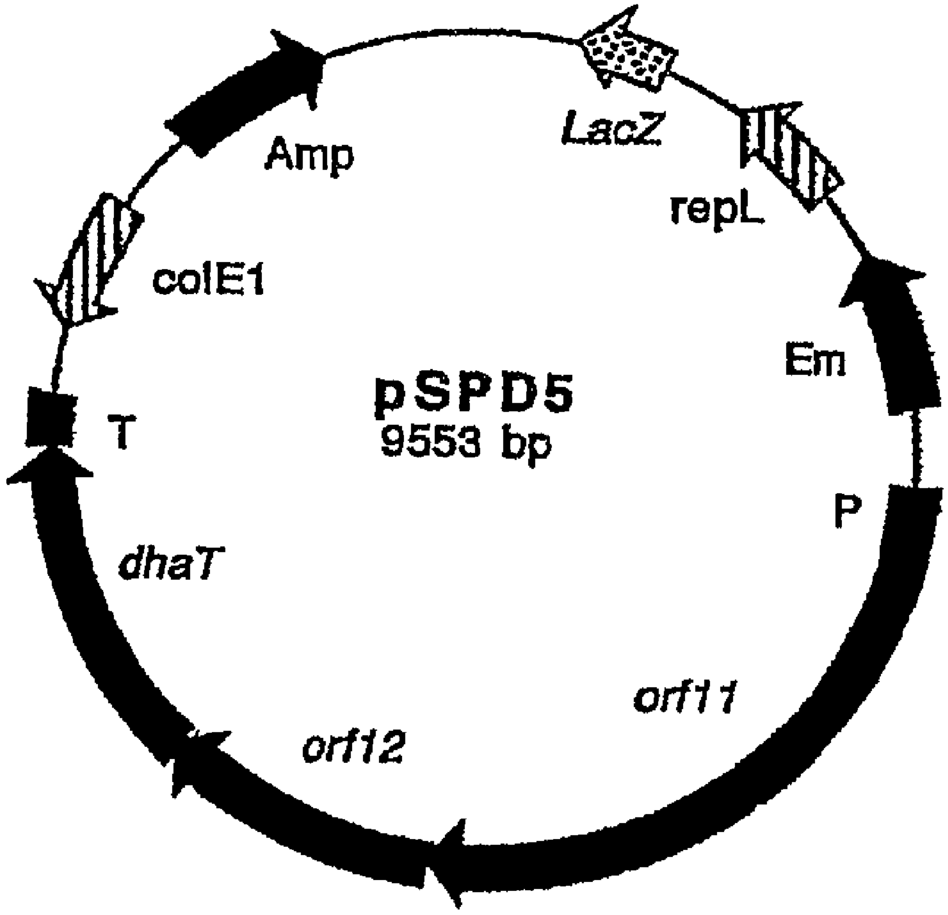
FIG. 2 illustrates the construction of the vector pSPD5

In parallel, the 4970 by BamHI-EheI fragment of the *E. coli/C. acetobutylicum* shuttle vector pSOS95 was purified on agarose gel then ligated to the PCR product of 4.6 kb. The recombinant vector thus constructed, called pSPD5 (FIG. 2), makes possible the constitutive expression of the genes orf11, orf12 and dhaT under the control of the promoter of the thiolase gene of *C. acetobutylicum.*

Example 2

Construction of the Expression Vectors pTPG(−) and pOPG

The vectors pTPG(−) and pOPG are vectors derived from the shuttle vector *E. coli-Clostridium* pTLH1 (HARRIS et al., 1999) which enables an adequate host cell to carry out the direct conversion of glucose to 1,3-propanediol. Basically, they allow the expression of the genes orf11, orf12 and dhaT of *C. butyricum* (1,3-propanediol operon) as well as that of the genes GPD1 and GPD2 of *S. cerevisae* coding respectively for glycerol-3-phosphate dehydrogenase and glycerol-3-phosphatase (artificial operon gly, carried by the plasmid pS2 (GELIS et al., 1999), derived from the plasmid pSOS95, which makes possible the conversion of glucose to glycerol in *E. coli* and *C. acetobutylicum*). These two plasmids are distinguished by the organization of these genes in two operons (1,3-propanediol and gly) in pTPG(−) and on the same operon in pOPG.

2.1. Construction of pTPG(−)

In a first step, the 4.9 kbp SalI fragment of the pSPD5 plasmid containing the entire 1,3-propanediol operon was purified on agarose gel, then ligated to the shuttle vector pTLH1 digested by SalI in order to obtain the pTLP plasmid of 10.6 kbp.

In parallel, the nucleotide primers OPGLY-D and OPGLY-R were synthesized in order to amplify the entire artificial operon gly.

The primer OPGLY-D includes the SmaI site as well as the beginning of the artificial operon gly. Its sequence is the following:

```
(SEQ ID NO: 11)
5'-GTTACCCGGGGCTCCTGCAGCTCGACTTTTTAAC-3'
```

The primer OPGLY-R hybridizes with the complementary strand and includes the SmaI site as well as the end of the artificial operon gly. Its sequence is the following:

```
(SEQ ID NO: 12)
5'-TTTCACCCGGGAAACAGCTATGACCATGATTACG-3'
```

An amplification reaction with the primers OPGLY-D and OPGLY-R was carried out on the plasmid pS2 under the following conditions:

annealing temperature for the primers: 48° C.;

duration of elongation: 3.5 minutes;

number of cycles: 10 cycles

The reaction made it possible to amplify a fragment of the expected size of 2.2 kbp.

Figure 3:
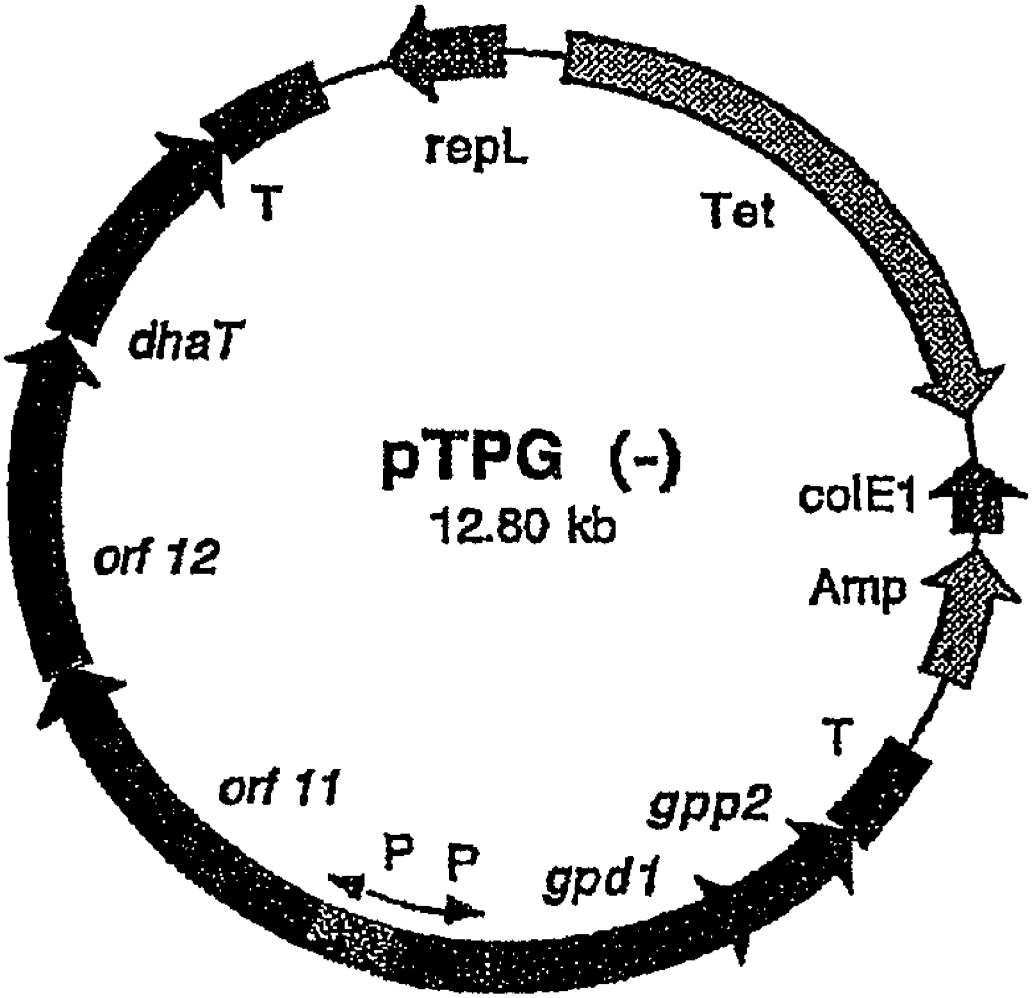
FIG. 3 illustrates the construction of the vector pTPG (–)

This amplified fragment was purified on agarose gel and digested by the enzyme SmaI, then ligated to the plasmid pTLP linearised by SmaI to furnish the plasmid pTPG(−) of 12.8 kbp (FIG. 3).

2.2. Construction of pOPG

In a first step, the 2.2 kbp PvuII-PstI fragment of the plasmid pS2 containing the entire glycerol operon was purified on agarose gel, then ligated to the 5.7 kbp SmaI-PstI fragment of the shuttle vector pTLH1 in order to obtain the plasmid pTLG1 of 7.9 kbp.

In parallel, the nucleotide primers dhaT-F and dhaT-R were synthesized in order to amplify the 5' end of the dhaT gene.

The primer DHAT-F includes the BamHI site as well as the central region of the dhaT gene. Its sequence is the following:

```
(SEQ ID NO: 13)
5'-TTGGATCCAGTATCTATAAATGATCCAATGC-3'
```

The primer DHAT-R hybridizes with the complementary strand and includes the BglII site as well as the end of the dhaT gene. Its sequence is the following:

```
(SEQ ID NO: 14)
5'-TTAGATCTTTTAAATAGTATTAATTAATAAGCAGCC-3'
```

An amplification reaction with the primers dhaT-F and dhaT-R was carried out on the plasmid pSPD5 under the following conditions:

annealing temperature for the primers: 48° C.;

duration of elongation: 1 minute;

number of cycles: 10 cycles

The reaction made it possible to amplify a fragment of the expected size of 0.65 kbp.

This amplified fragment was purified on agarose gel and digested by the enzymes BamHI and BglII, then ligated to the plasmid pTLG1 linearised by BamHI to furnish the plasmid pTPG of 8.55 kbp.

Figure 4:
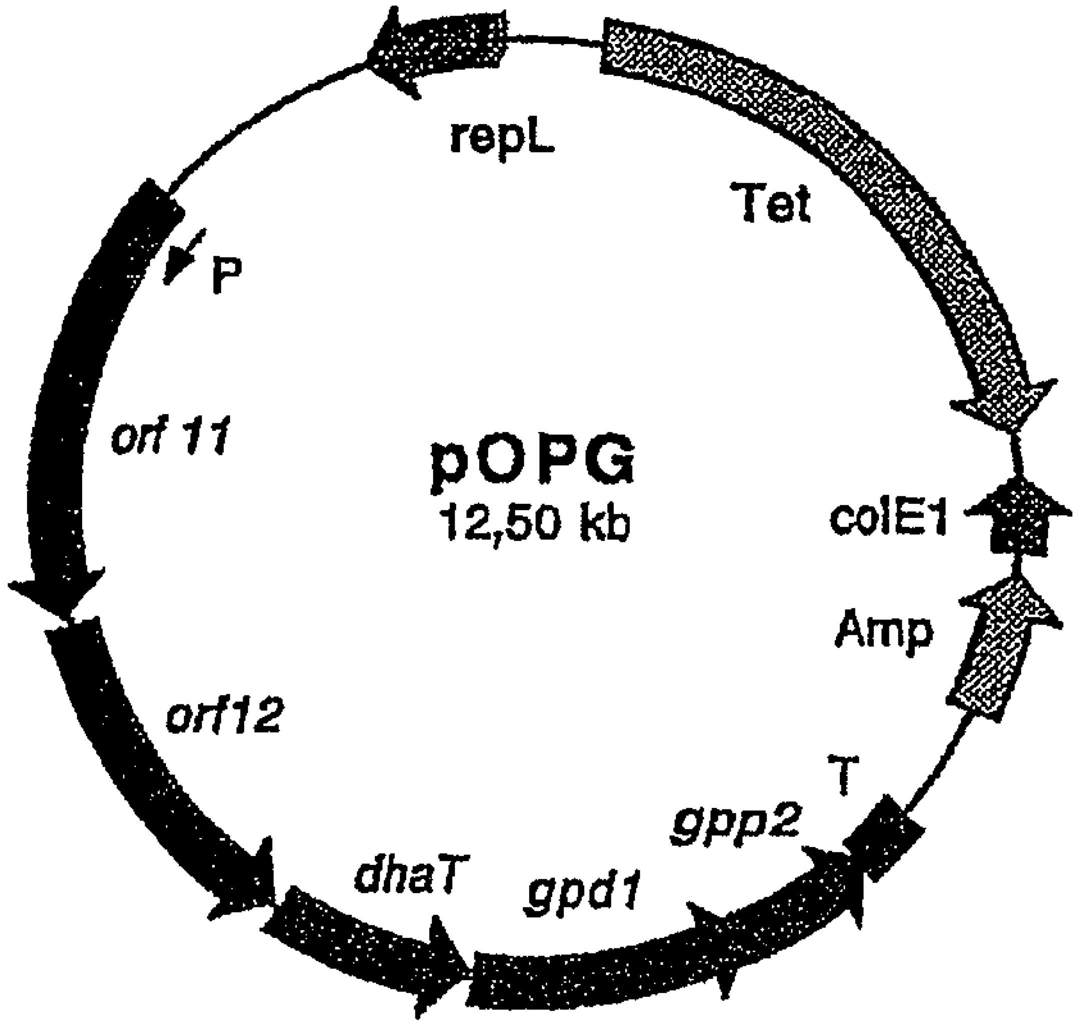
FIG. 4 illustrates the construction of the vector pOPG
Figure 5:
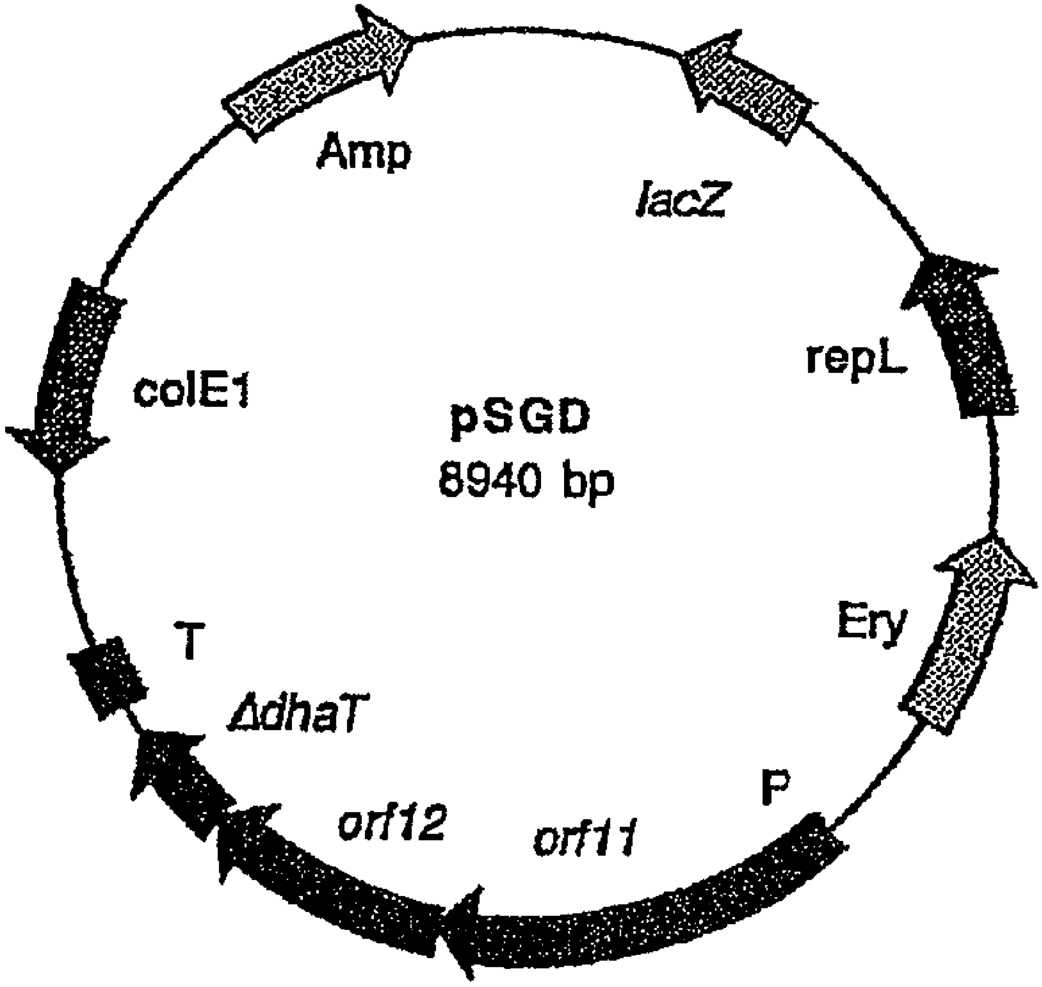
FIG. 5 illustrates the construction of the vector pSGD
Figure 6:
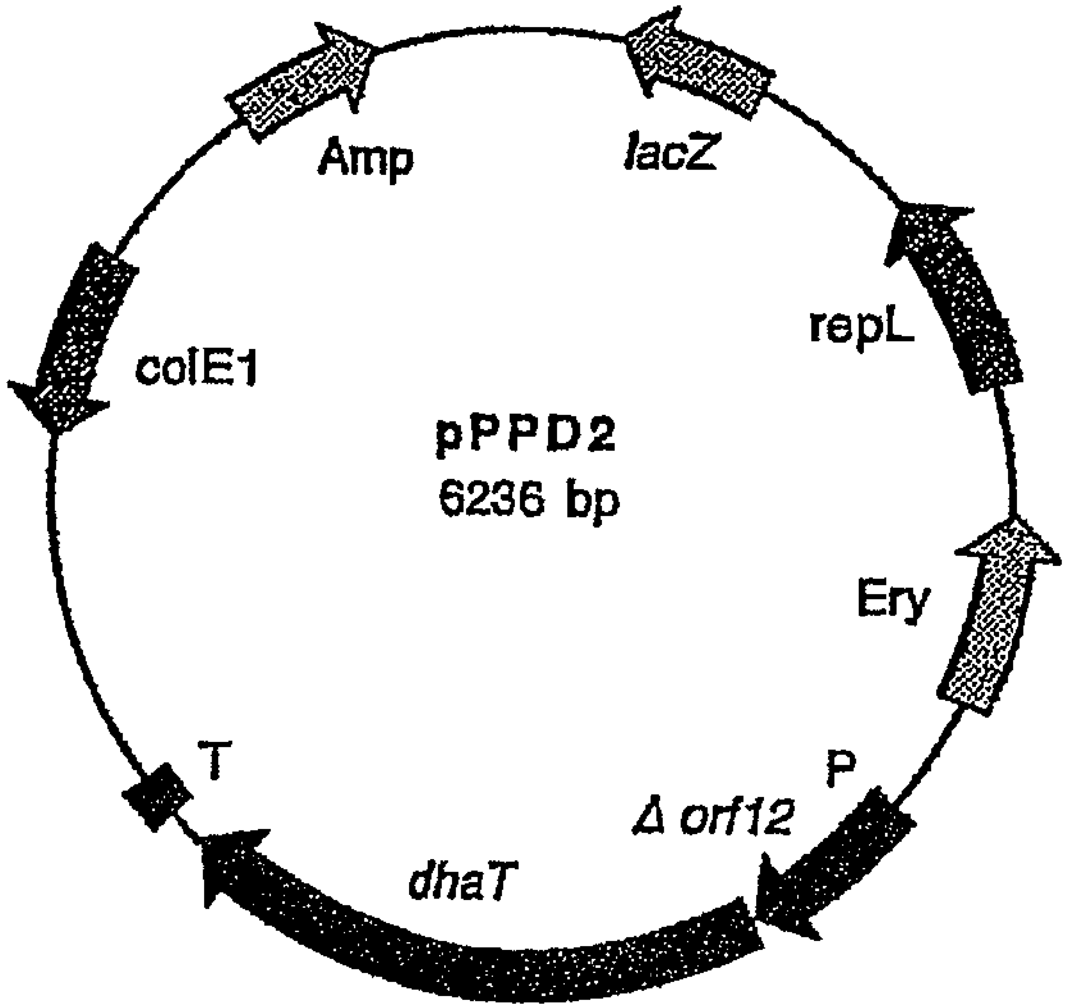
FIG. 6 illustrates the construction of the vector pPPD2

In a last step, the 4.0 kbp BamHI-SbfI fragment of the plasmid pSPD5 was purified on agarose gel then ligated to the 8.55 kbp BamHI-SbfI fragment of the plasmid pTPG in order to obtain the plasmid pOPG of 12.55 kbp (FIG. 4).

Example 3

Construction of the Expression Vector pSGD

The vector pSGD is derived from the plasmid pSPD5.

Basically, the vector pSGD expresses functionally orf11 and orf12 (coding respectively for the first and second protein subunits of glycerol dehydratase) and contains a deletion in the region coding for DHAT (1,3-propanediol dehydrogenase).

The vector pSPD5 was subjected to digestion by the restriction enzyme SbfI and the 4082 by fragment purified on agarose gel.

Digestion of the vector pSOS95 was then carried out by means of the restriction enzyme PstI and the 4858 by fragment was purified on agarose gel.

These two fragments were then ligated in order to obtain the plasmid pSGD.

Example 4

Construction of the Expression Vector pPPD2

The vector pPPD2 is a vector derived from the plasmid pSPD5 capable of expressing the dhat gene (coding for the 1,3-propanediol dehydrogenase) and in which orf11 (coding for the first subunit of the glycerol dehydratase has been entirely deleted as well as 100 by at the 5' end of orf12 (coding for the second subunit of the glycerol dehydratase).

The vector pSPD5 was first digested simultaneously by the restriction enzymes BamHI and MfeI.

The 6326 by BamHI-MfeI fragment obtained by double digestion with the aid of the corresponding restriction endonucleases was subjected to a treatment in the presence of the T4 DNA polymerase in order to obtain blunt ends.

The fragment was then subjected to relegation on itself in order to obtain the plasmid pPPD2.

Example 5

Figure 7:
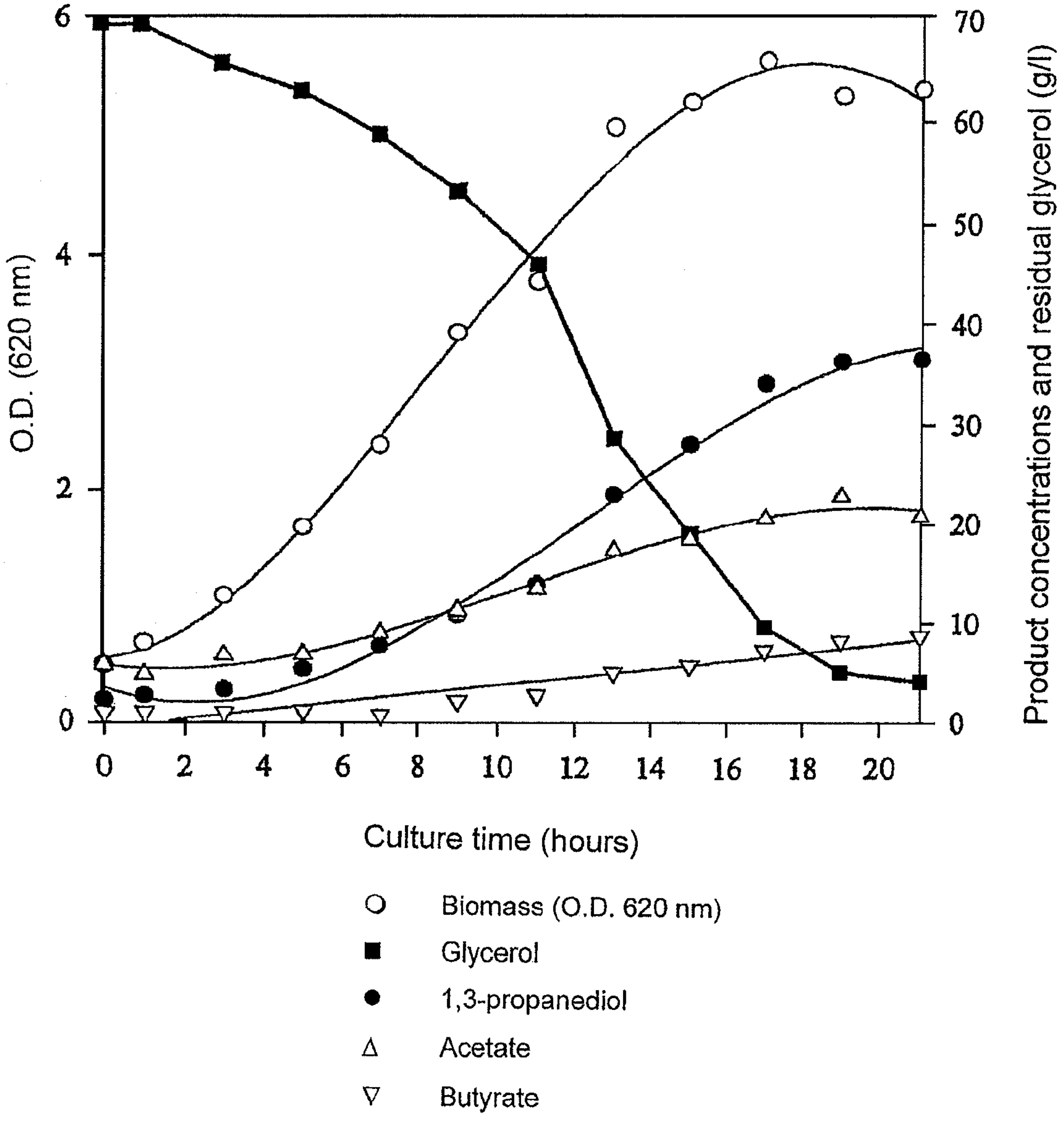
FIG. 7 illustrates the production of 1,3-propanediol from glycerol by the *Clostridium acetobutylicum* strain DG1 (pSPD5).

Expression of the 1,3-propanediol Operon in *Clostridium acetobutylicum* DG1 Grown on Glycerol The *Clostridium acetobutylicum* DGI strain transformed with the plasmid pSPD5 as described in the Materials and Methods section was placed in culture in the presence of glycerol for defined times and different parameters were monitored during fermentation:

- bacterial growth was monitored by measurement of the optical density at the wavelength of 620 nanometers and is shown on FIG. 7 by the open circles;
- the glycerol concentration was monitored throughout the fermentation and is shown in FIG. 7 by filled squares;
- the synthesis of 1,3-propanediol was also monitored throughout the fermentation and is shown by filled circles;
- similarly the acetate and butyrate concentrations were measured throughout fermentation and are shown in FIG. 7 by triangles and inverted triangles, respectively.

The results shown in FIG. 7 show that a significant quantity of 1,3-propanediol is synthesized by the *Clostridium acetobutylicum* DGI strain transformed by the plasmid pSPD5 after the first four hours of culture. After 20 hours of fermentation, it is possible to observe the production of 38 g/l of 1,3-propanediol. The production of 1,3-propanediol reaches a plateau about 18 hours after the beginning of fermentation, this plateau of production being essentially due to the fact that almost all of the initial glycerol has been consumed by the transformed bacterium.

It is important to note that the *C. acetobutylicum* DG1 strain transformed by the control plasmid pIMP1 not containing the regions coding for the glycerol dehydratase and the 1,3-propanediol dehydrogenase (Memmerlstein, 1992) does not grow on the culture medium with glycerol as sole carbon source and hence does not produce 1,3-propanediol (Table 1).

Example 6

Expression of the 1,3-propanediol Operon in *Escherichia coli* DH5α Grown on Glycerol An *Escherichia coli* DH5α strain was transformed with the vector pSPD5 as described in the Materials and Methods section.

The *Escherichia coli* strain transformed with the plasmid pSPD5 was grown in anaerobiosis on LB medium supplemented with glycerol (40 g/l) and erythromycin (300 μg/ml), the production of 1,3-propanediol was measured at defined times.

Figure 8:
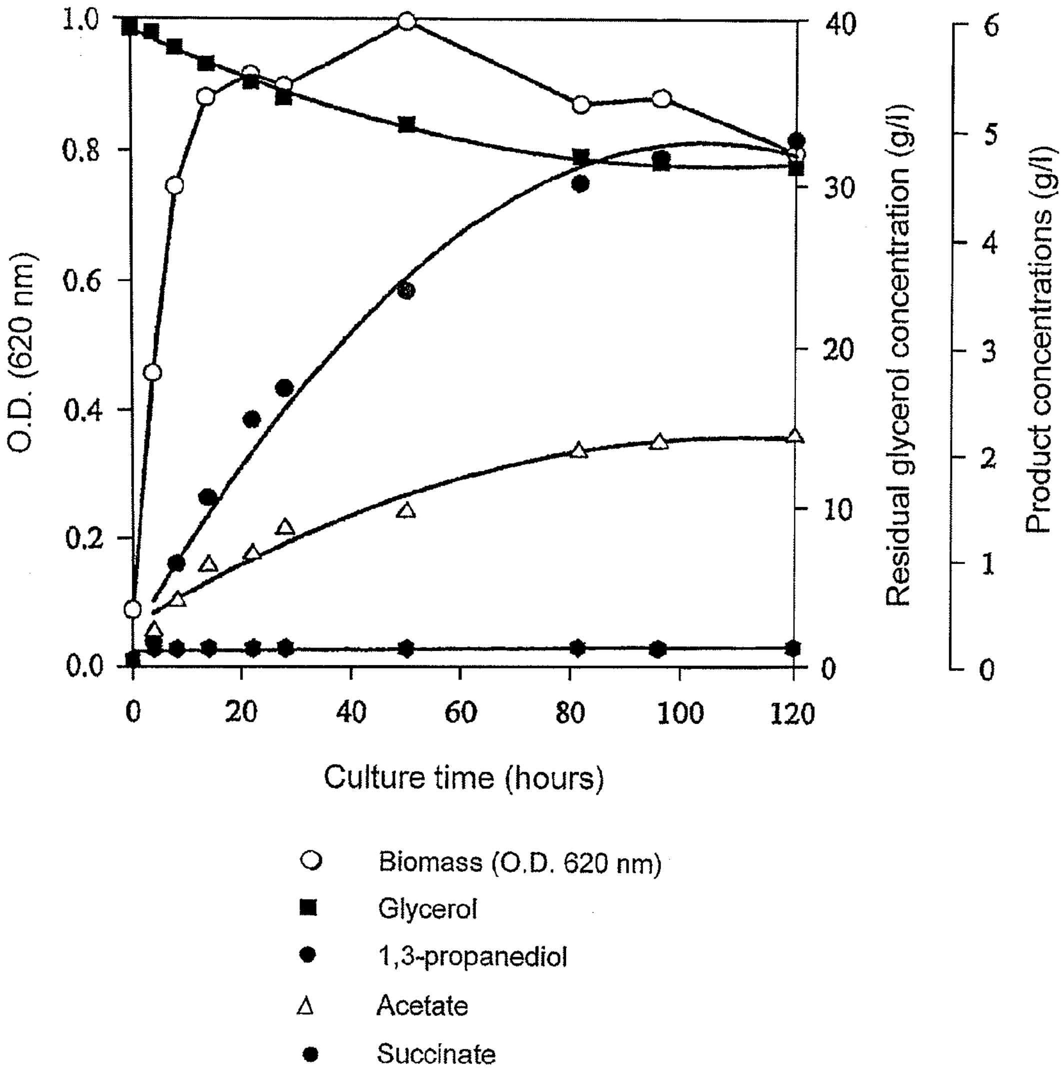
FIG. 8 illustrates the production of 1,3-propanediol from glycerol by the *E. coli* strain DH5α transformed by the vector pSPD5 and grown under anaerobiosis.

The results are summarized in FIG. 8.

The results of FIG. 8 show that a significant amount of 1,3-propanediol is produced right from the start of fermentation. After 80 hours of fermentation, a production of about 4.5 g/l of 1,3-propanediol can be observed.

The control strain *E. coli* DH5α[pIMP1] grown on the same medium does not lead to the production of 1,3-propanediol (Table 1).

TABLE 1

Production of 1,3-propanediol by recombinant strains grown at pH 6.5 in the presence of glycerol under anaerobic conditions

| | 1,3-propanediol (g/l) |
|---|---|
| *E. coli* DH5α (pIMP1) | 0 |
| *E. coli* DH5α (pSPD5) | 4.5 |
| *C. acetobutylicum* DG1 (pIMP1) | No growth |
| *C. acetobutylicum* DG1 (pSPD5) | 38 |

The results of Table 1 show that a significant production of 1,3-propanediol (about 5 g/l) is obtained with the *Escherichia coli* DH5α strain transfected by the plasmid pSPD5, whereas the *E. coli* strain transfected with the control plasmid pIMP1 does not produce a detectable quantity of 1,3-propanediol.

With the construction pSPD5, a quantity of 1,3-propanediol is observed with the *Clostridium acetobutylicum* strain approximately 7.6 fold higher than with the *Escherichia coli* DH5α strain. This is mainly due to the fact that the regulatory signals of the plasmid pSPD5 were optimised for the expression of the 1,3-propanediol operon in *Clostridium acetobutylicum.*

Regulatory signals such as a very active promoter in *Escherichia coli* are capable of making possible the production of as large a quantity of 1,3-propanediol in *Escherichia coli* as that observed in *Clostridium acetobutylicum.*

Example 7

Expression of the 1,3-propanediol Operon in Wild-Type *Clostridium butyricum* Grown on Glycerol The *Clostridium butyricum* strain VPI 1718 was grown in the presence of glycerol and the synthesis of 1,3-propanediol was measured at defined times throughout fermentation.

Figure 9:
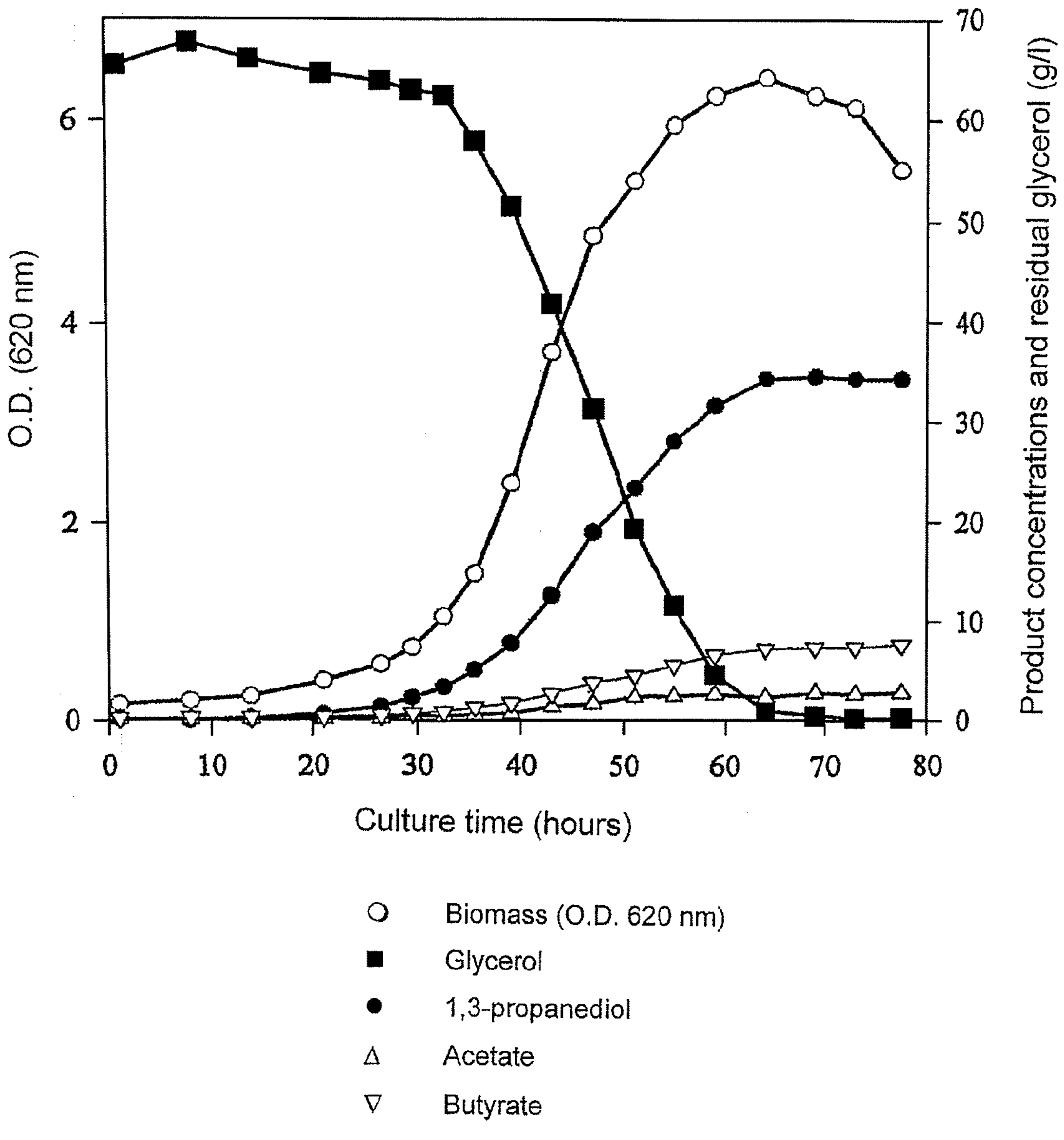
FIG. 9 illustrates the production of 1,3-propanediol from glycerol by the non-recombinant *Clostridium butyricum* strain VPI 1718.

The results are presented in FIG. 9.

The results of FIG. 9 show that the production of 34 g/l of 1,3-propanediol is observed after 60 hours of fermentation.

If reference is made to the results shown in FIG. 7, it can be observed that the production of 1,3-propanediol by the *Clostridium acetobutylicum* DG1 strain transformed by the plasmid pSPD5 is much more rapid (22 hours as opposed to 60 hours) and higher than the production of 1,3-propanediol obtained with the *Clostridium butyricum* strain naturally expressing the coenzyme B12-independent glycerol dehydratase and the 1,3-propanediol dehydrogenase according to the invention.

Moreover, the levels of catalytic activity, expressed in units per mg, of glycerol dehydratase and 1,3-propanediol dehydrogenase were measured in both *Clostridium acetobutylicum* and *Clostridium butyricum*.

The results are shown in the DG1[pSPD5] Table 2 below

TABLE 2

Levels of enzymes implicated in the production of 1,3-propanediol in the recombinant *C. acetobutylicum* strains and *C. butyricum*.

| | Glycerol dehydratase (U/mg) | 1,3-propanediol dehydrogenase (U/mg) |
|---|---|---|
| *C. acetobutylicum* DG1 (PSPD5) Growth on glycerol | 3.5 | 2.4 |
| *C. acetobutylicum* DG1 (pIMP1) Growth on glucose | 0.01< | 0.005< |
| *C. butyricum* Growth on glycerol | 0.45 | 0.56 |

The results presented in Table 2 indicate that the levels of activity of the glycerol dehydratase and the 1,3-propanediol dehydrogenase expressed in the *Clostridium acetobutylicum* strain transformed by the plasmid pSPD5 are much higher (7.8 and 4.3 fold higher, respectively) than the levels of glycerol dehydratase and 1,3-propanediol dehydrogenase activity expressed by the *Clostridium butyricum* strain naturally producing these enzymes.

As control, a *Clostridium acetobutylicum* strain transformed with the plasmid pIMPI not containing the regions coding for the glycerol dehydratase and the 1,3-propanediol dehydrogenase does not produce detectable quantities of these two enzymes, which shows clearly that the activity observed in the strain transformed by the plasmid pSPD5 is solely due to the expression of the 1,3-propanediol operon according to the invention.

The results presented in Table 2 clearly demonstrate the value of transforming a strain of micro-organism not naturally producing glycerol dehydratase and 1,3-propanediol dehydrogenase according to the invention with a recombinant vector such as the vector pSPD5 because it is possible in this case for example by the use of appropriate promoters to obtain levels of expression which are never attained naturally.

Example 8

Expression of the Genes of the 1,3-propanediol Operon in *Saccharomyces cerevisia*

A. Materials and Methods

A.1 Materials

| MSL MEDIUM | |
|---|---|
| SALTS | g/l |
| $(NH_4)_2SO_4$ | 5 |
| $MgSO_4 \cdot 7H_2O$ | 0.5 |
| $KH_2PO_4$ | 1 |
| NaCl | 0.1 |
| $CaCl_2 \cdot 2H_2O$ | 0.1 |

-continued

| MSL MEDIUM | |
|---|---|
| | mg/l |
| VITAMINS | |
| d-biotin | 0.02 |
| Ca D(+) pantothenate | 0.4 |
| myo-inositol | 2.0 |
| thiamine HCl | 0.4 |
| pyridoxine HCl | 0.4 |
| p-aminobenzoic acid | 0.2 |
| folic acid | 0.02 |
| niacin | 0.4 |
| riboflavin | 0.2 |
| TRACE ELEMENTS | |
| $ZnSO_4 \cdot 7H_2O$ | 0.4 |
| $MnSO_4$ | 0.4 |
| $CuSO_4 \cdot 5H_2O$ | 0.04 |
| $Na_2MoO_4 \cdot 2H_2O$ | 0.2 |
| $FeCl_3 \cdot 6H_2O$ | 0.2 |
| $H_3BO_3$ | 0.5 |
| KI | 0.1 |
| | g/l |
| CARBON SOURCE | |
| glucose | 10 |
| glycerol | 10 |
| AA (drop-out) | |
| L-Arg | 0.02 |
| Thre | 0.05 |
| L-Tryp | 0.04 |
| L-Isoleu | 0.06 |
| Lys | 0.04 |
| Met | 0.01 |
| Phe | 0.06 |
| Tyr | 0.05 |
| Adenine | 0.01 |
| Ergosterol | 0.01 |
| Tween 80 | 0.42 |

A.2. Methods

The genes orf11, orf12 and dhat were individually amplified by means of PCR after introducing a SmaI site at the 5' end and an ApaI site at the 3' end by the use of primers. Through the agency of these two restriction sites each gene was then introduced into the vector pYGK (CROUX and SOUCAILLE, 1999) making it possible to construct an expression cassette under the control of the promoter of the PGK gene and of the terminator of the CYC1 gene. The three genes in their expression cassette were then cut out from each of the vectors previously obtained (pYGK11, pYGK12 and pYGKT) by NotI-SacII digestion and introduced into three multimeric vectors of the family pRS42x which differ by the nature of their selection marker (HIS3 for pRS423, LEU2 for pRS425 and URA3 for pRS426) previously digested by the same restriction enzymes. Each of the three plasmids obtained (pRSGK11, pRSGK12 and pRSGKT) was then introduced into the *S. cerevisae* JF624 (leu2, ura3 lys2 trp1 his3) strain and selected by complementation with the 3 auxotrophies of this strain. The *S. cerevisae* JF624 (pRSGK11, pRSGK12, pRSGKT) strain and the control strain *S. cerevisae* JF624 (PRS423, PRS425, pRS426) were then grown in anaerobiosis for 36 hours in the MSL medium.

B. Results

The results of the expression of the genes of the 1,3-propanediol operon in the *S. cerevisae* JF624 strains described in paragraph A.2 above are presented in Table 3 below.

The results in Table 3 show that the *S. cerevisae* JF624 strain which contains the inserts of the genes orf11, orf12 and dhat inserted respectively in the pRSGK11, pRSGK12 and pRSGKT plasmids is capable of producing 1,3-propanediol from a glycerol source without the addition of vitamin B12.

TABLE 3

| | Ethanol (g/l) | 1,3-propanediol (g/l) |
|---|---|---|
| *S. cerevisae* JF624 (pRS423, pRS425, pRS426 | 4.5 | 0 |
| *S. cerevisae* JF624 (pRSGK11, pRSGK12, pRSGKT) | 4.8 | 0.1 |

Example 9

Expression of the 1,3-propanediol Operon in *Clostridium acetobutylicum* DG1 [pSPD5] Grown on Glucose The *Clostridium acetobutylicum* DG1 strain transformed by the plasmid pSPD5 as described in the Materials and Methods section was grown in the presence of glucose as sole carbon source and different parameters were monitored during the fermentation.

Figure 10:
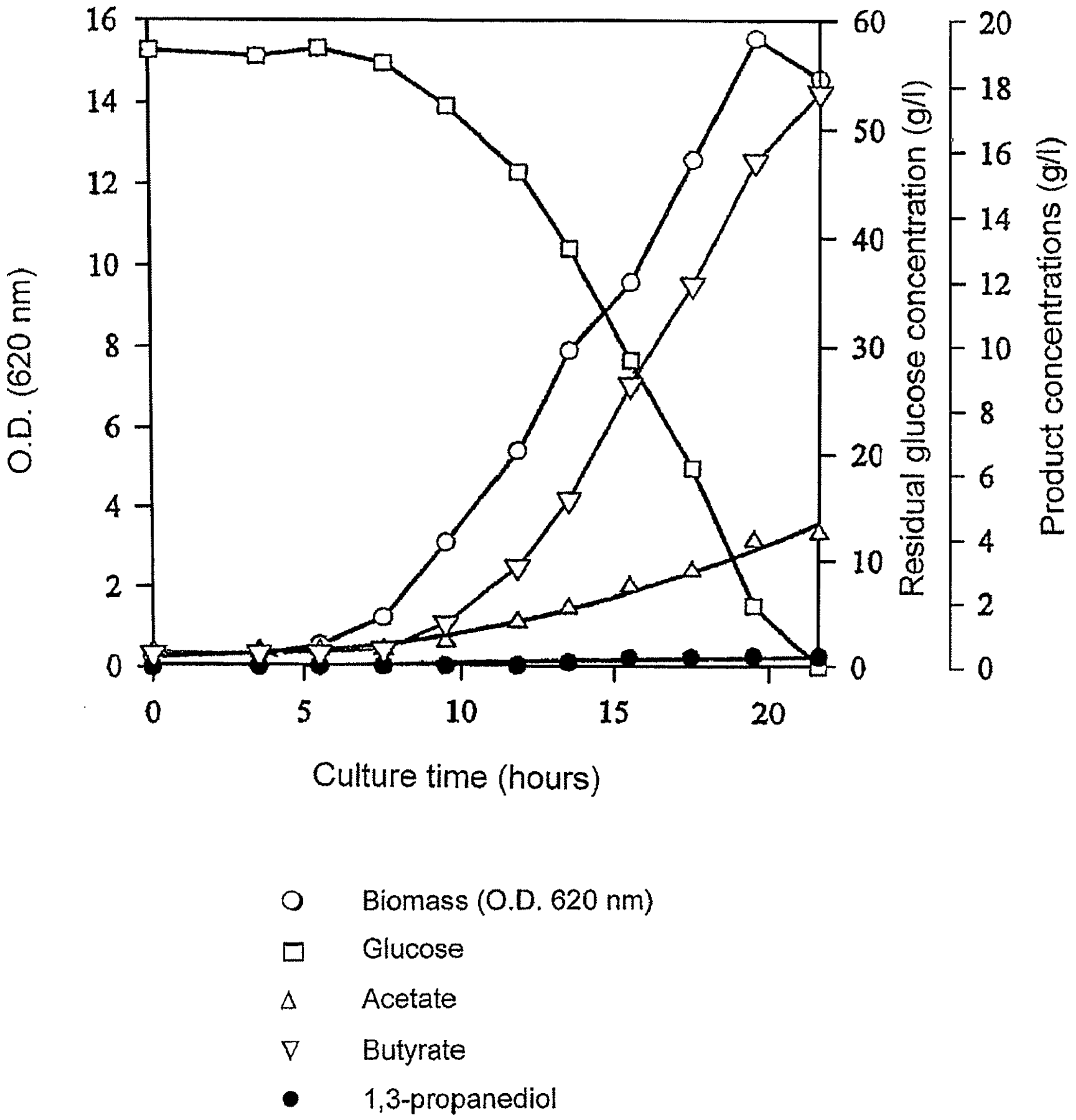
FIG. 10 illustrates the production of 1,3-propanediol from glucose by the *Clostridium acetobutylicum* strain DG1 [pSPD5].

The results are presented in FIG. 10.

The results in FIG. 10 show a low level (0.3 g/l) of synthesis of 1,3-propanediol whereas all of the glucose was consumed. This production, due to the presence of a low concentration of intracellular glycerol in *Clostridium acetobutylicum* DG1 [pSPD5] demonstrates however the feasibility of a direct conversion process of glucose to 1,3-propanediol in a strain carrying the genes claimed by the present invention.

Example 10

Expression of the 1,3-propanediol Operon in *Bacillus subtilis* 168 [pSPD5] Grown on Glycerol The *Bacillus subtilis* 168 strain transformed by the plasmid pSPD5 as described in the Materials and Methods section was grown on LB medium+10 g/l glycerol+20 mM nitrate+2 ng/ml erythromycin in anaerobiosis and compared to the same strain transformed by the control plasmid pIMP1.

The results are presented in Table 4 below

TABLE 4

| | Acetate (g/l) | 2,3-butanediol (g/l) | 1,3-propanediol (g/l) |
|---|---|---|---|
| *B. subtilis* 168 (pSPD5) | 0.84 | 1.2 | 0 |
| *B. subtilis* 168 (pSPD5) | 0.9 | 1.0 | 0.2 |

The results in Table 3 show that the expression of the 1,3-propanediol operon in *B. subtilis* makes possible the production of 1,3-propanediol from glycerol without the addition of vitamin B12.

Example 11

Conversion of Glucose to 1,3-propanediol by *E. coli* NZN 111 [pTPG]

The plasmid pTPG(−) and the control plasmid pTLH1 were introduced into the *E. coli* NZN 111 (pfl:cat, Idh:kan) strain, a strain incapable of producing formate and lactate in anaerobiosis. These two recombinant strains were then grown anaerobically for 48 hours in the LB medium+glucose+10 μg/ml of tetracycline without regulation of pH. The results presented in Table 5 show that *E. coli* can produce significant quantities of 1,3-propanediol from glucose after transformation by the plasmid pTPG.

TABLE 5

| | Acetate g/l | Succinate (g/l) | Glycerol (g/l) | 1,3 propanediol (g/l) |
|---|---|---|---|---|
| *E. coli* NZN111 (pTLH1) | 0.15 | 0.4 | 0 | 0 |
| *E. coli* NZN111 (pTPG) | 1.25 | 0.2 | 2.1 | 0.7 |

BIBLIOGRAPHIC REFERENCES

Gelis, C. et al., 1999—Unpublished.

Hames B D and Higgins S J, 1985, "Nucleic acid hybridization: a practical approach", Hames and Higgins Ed., IRL Press, Oxford.

Harris, L. M. et al., 1999—Unpublished.

Houbenweyl, 1974, in Methode der Organischen Chemie, E. Wunsch Ed., Volume 15-I et 15-II, Inoue et al., 1990, Gene, 96, 23-28.

Kohler G. and Milstein C., 1975, Nature, 256:495.

Lee S. Y. et al., 1992, Biotech Lett., 14: 427-432.

Leger O J, et al., 1997, Hum Antibodies, 8(1): 3-16

Maguin E. et al., 1992, J. Bacteriol., 174: 5633-5638.

Martineau P, Jones P, Winter G, 1998, J Mol Biol, 280(1): 117-127

Memmerlstein D. L., 1992, PhD Thesis, Northwestern University, Evanston, Ill., USA.

Merrifield R B, 1965a, Nature, 207(996): 522-523.

Merrifield R B., 1965b, Science, 150(693): 178-185.

Reimann K A, et al., 1997, AIDS Res Hum Retroviruses. 13(11): 933-943

Sambrook, J. Fritsch, E. F., and T. Maniatis. 1989. Molecular cloning: a laboratory manual. 2ed.

Soucaille P. et Papoutsakis, 1996, Unpublished.

Truffaut N. et al., 1989, FEMS Microbiol. Lett., 58: 15-20.

Williams D. R. et al., 1990, J. Gen. Microbiol., 136: 819-826

Yannish-Perron C. et al., 1985, Gene, 33: 103-119.

The invention claimed is:

1. A recombinant dimeric glycerol dehydratase comprising: (a) a first polypeptide having at least 90% amino acid identity with the amino acid sequence of SEQ ID NO: 6, and (b) a second polypeptide having at least 95% amino acid identity with the amino acid sequence of SEQ ID NO: 7.

2. The recombinant dimeric glycerol dehydratase according to claim 1, wherein the first polypeptide is encoded by a first polynucleotide having at least 95% nucleotide identity with the polynucleotide of sequence SEQ ID NO: 1.

3. The recombinant dimeric glycerol dehydratase according to claim 1, wherein the second polypeptide is encoded by a second polynucleotide having at least 95% nucleotide identity with the polynucleotide of sequence SEQ ID NO: 2.

4. A recombinant dimeric glycerol dehydratase comprising (a) a first polypeptide consisting of the amino acid sequence of SEQ ID NO: 6, and (b) a second polypeptide consisting of the amino acid sequence of SEQ ID NO: 7.

5. The recombinant dimeric glycerol dehydratase according to claim 4, wherein the first polypeptide is encoded by a first polynucleotide of sequence SEQ ID NO: 1.

6. The recombinant dimeric glycerol dehydratase according to claim 4, wherein the second polypeptide is encoded by a second polynucleotide of sequence SEQ ID NO: 2.

* * * * *